(12) United States Patent
Liu et al.

(10) Patent No.: US 9,506,050 B2
(45) Date of Patent: Nov. 29, 2016

(54) POLYPEPTIDES HAVING ENDOGLUCANASE ACTIVITY AND POLYNUCLEOTIDES ENCODING SAME

(71) Applicant: Novozymes A/S, Bagsvaerd (DK)

(72) Inventors: Ye Liu, Beijing (CN); Lan Tang, Beijing (CN); Weijian Lai, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/647,297

(22) PCT Filed: Dec. 24, 2013

(86) PCT No.: PCT/CN2013/090355
§ 371 (c)(1),
(2) Date: May 26, 2015

(87) PCT Pub. No.: WO2014/101753
PCT Pub. Date: Jul. 3, 2014

(65) Prior Publication Data
US 2015/0299682 A1    Oct. 22, 2015

Related U.S. Application Data

(60) Provisional application No. 61/760,228, filed on Feb. 4, 2013, provisional application No. 61/760,230, filed on Feb. 4, 2013, provisional application No. 61/760,226, filed on Feb. 4, 2013.

(30) Foreign Application Priority Data

Dec. 24, 2012 (WO) ................ PCT/CN2012/087336
Dec. 24, 2012 (WO) ................ PCT/CN2012/087339
Dec. 24, 2012 (WO) ................ PCT/CN2012/087345

(51) Int. Cl.
*C12N 9/42* (2006.01)
*C12P 21/02* (2006.01)
*D06M 16/00* (2006.01)

(52) U.S. Cl.
CPC ..... *C12N 9/2437* (2013.01); *C12Y 302/01004* (2013.01); *D06M 16/003* (2013.01)

(58) Field of Classification Search
None
See application file for complete search history.

(56) References Cited

U.S. PATENT DOCUMENTS 7,256,032 B2 *  8/2007  Valtakari ............ C11D 3/38636
                                                         426/20

FOREIGN PATENT DOCUMENTS

| CN | WO 2012089024 A1 * | 7/2012 | ......... D06M 16/003 |
| WO | 96/29397 A1 | 9/1996 | |
| WO | 2004/053039 A2 | 6/2004 | |
| WO | 2010/076388 A1 | 7/2010 | |
| WO | 2012/106824 A1 | 8/2012 | |

OTHER PUBLICATIONS

Berka et al., UniProt Accession No. G2QVH7 (2011).
Berka et al., UniProt Accession No. G2R3B9 (2011).
Berka et al., GenBank Accession No. XP_003651003 (2012).
Koga et al., GeneSeqP Accession No. AEA35116 (2005).
Koga et al., UniProt Accession No. B5BNY1 (2008).
Lai et al., GeneSeqP Accession No. AZX3356 (2012).
Anonymous, NCBI Database accession No. XP002757334 (2012).
Anonymous, NCBI Database accession No. XP002757335 (2012).
Anonymous, NCBI Database accession No. XP002757336 (2012).
Henrissat et al., Biochem. J., vol. 293, No. 3, pp. 781-788 (1993).
Shimonaka et al, Biosci. Biotechnol. Biochem., vol. 70, No. 4, pp. 1013-1016 (2006).
Shimonaka et al, Biosci. Biotechnol. Biochem., vol. 70, No. 10, pp. 2460-2466 (2006).

* cited by examiner

*Primary Examiner* — David J Steadman
(74) *Attorney, Agent, or Firm* — Elias Lambiris

(57) ABSTRACT

Provided are isolated polypeptides having endoglucanase activity, catalytic domains, carbohydrate binding modules and polynucleotides encoding the polypeptides, catalytic domains or carbohydrate binding modules. Also provided are nucleic acid constructs, vectors and host cells comprising the polynucleotides as well as methods of producing and using the polypeptides, catalytic domains or carbohydrate binding modules.

20 Claims, 3 Drawing Sheets

SEQUENCE LISTING

```
<160> NUMBER OF SEQ ID NOS: 13

<210> SEQ ID NO 1
<211> LENGTH: 1026
<212> TYPE: DNA
<213> ORGANISM: Humicola hyalothermophila
<220> FEATURE:
<221> NAME/KEY: sig_peptide
<222> LOCATION: (1)..(63)
<220> FEATURE:
<221> NAME/KEY: exon
<222> LOCATION: (1)..(89)
<220> FEATURE:
<221> NAME/KEY: exon
<222> LOCATION: (154)..(402)
<220> FEATURE:
<221> NAME/KEY: exon
<222> LOCATION: (466)..(988)

<400> SEQUENCE: 1 atg cgt tct tct cct atc ctt cgc aaa gcc gtg gca gct gcc ctc cct      48
Met Arg Ser Ser Pro Ile Leu Arg Lys Ala Val Ala Ala Ala Leu Pro
1               5                   10                  15
```

```
ctg ggt gct tat gcc gca agt ggc aat ggc cag tcc acg ag          89
Leu Gly Ala Tyr Ala Ala Ser Gly Asn Gly Gln Ser Thr Arg
        20                  25                  30 gtaatcacat atttcctttg gtcttacctg ctggtcgtgt ttagccaatg ctaaccaacc    149 caag g tac tgg gac tgc tgc aag ccc tcc tgc gcc tgg cca gag aag     196
      Tyr Trp Asp Cys Cys Lys Pro Ser Cys Ala Trp Pro Glu Lys
                     35                  40 gct gcc gtg agc cag cct gtc tat gcc tgc gac gcc aac ttc cag cgc   244
Ala Ala Val Ser Gln Pro Val Tyr Ala Cys Asp Ala Asn Phe Gln Arg
45                  50                  55                  60 atc agc gac ccc ttg gtc agc tct ggc tgt gac ggc ggc cag gcc ttt   292
Ile Ser Asp Pro Leu Val Ser Ser Gly Cys Asp Gly Gly Gln Ala Phe
                65                  70                  75 tcg tgc gcc gat cac agc ccg tgg gcg ttg aac gac aac ctg tcc tac   340
Ser Cys Ala Asp His Ser Pro Trp Ala Leu Asn Asp Asn Leu Ser Tyr
                80                  85                  90 gga ttt gcg gct aca gct ctt gcc gga ggc acg gaa gcc tct tgg tgc   388
Gly Phe Ala Ala Thr Ala Leu Ala Gly Gly Thr Glu Ala Ser Trp Cys
                95                  100                 105 tgc gca tgc tat gc gtgagtacca tcaaggacaa acctcagctc gcataaacac    442
Cys Ala Cys Tyr Ala
        110 acagcgcagc taacccgtcc cag g ctc acc ttc act tcc ggc cct gtg gca   493
                           Leu Thr Phe Thr Ser Gly Pro Val Ala
                                   115                 120 ggc aag acc atg gtt gtc caa tcg acc agc acc ggc ggc gac ctc ggc   541
Gly Lys Thr Met Val Val Gln Ser Thr Ser Thr Gly Gly Asp Leu Gly
                125                 130                 135 aac aac cac ttc gat ctc aac atc ccc ggc ggc ggc gtc ggc ctc ttc   589
Asn Asn His Phe Asp Leu Asn Ile Pro Gly Gly Gly Val Gly Leu Phe
140                 145                 150 gac gga tgc acg ccc cag ttc ggc ggt ctg ccc ggc gcc cag tac ggc   637
Asp Gly Cys Thr Pro Gln Phe Gly Gly Leu Pro Gly Ala Gln Tyr Gly
155                 160                 165                 170 ggc att tcg tcg cgc agc gaa tgc gac tcg ttc ccc gag ccc ctc aag   685
Gly Ile Ser Ser Arg Ser Glu Cys Asp Ser Phe Pro Glu Pro Leu Lys
                175                 180                 185 gca ggc tgc tac tgg cgc ttc gac tgg ttc cag aac gcc gac aac ccg   733
Ala Gly Cys Tyr Trp Arg Phe Asp Trp Phe Gln Asn Ala Asp Asn Pro
                190                 195                 200 agc ttc acc ttc gag cag gtc cag tgc ccg gac gag ctc gtc gcg cgc   781
Ser Phe Thr Phe Glu Gln Val Gln Cys Pro Asp Glu Leu Val Ala Arg
                205                 210                 215 acc ggt tgc cgc cgc aac gac gac ggc aac ttc ccc gtc ttc acg cct   829
Thr Gly Cys Arg Arg Asn Asp Asp Gly Asn Phe Pro Val Phe Thr Pro
220                 225                 230 ccc gcc ggc ggc aat gac ggc gag cag ccg ggc aac ccc ggc gac tgc   877
Pro Ala Gly Gly Asn Asp Gly Glu Gln Pro Gly Asn Pro Gly Asp Cys
235                 240                 245                 250 gtc gcg caa aag tgg gag cag tgc ggc ggc agt ggc ttc tcg ggc tgc   925
Val Ala Gln Lys Trp Glu Gln Cys Gly Gly Ser Gly Phe Ser Gly Cys
                255                 260                 265 acg acc tgc gcc agt ggc tcg acc tgc cag gtg gtg aac gag tgg tac   973
Thr Thr Cys Ala Ser Gly Ser Thr Cys Gln Val Val Asn Glu Trp Tyr
                270                 275                 280 tct cag tgt gtg taa tgttgttggg gagtactgtt ctgctgaggt cagatggc    1026
Ser Gln Cys Val
        285
```

<210> SEQ ID NO 2
<211> LENGTH: 286
<212> TYPE: PRT
<213> ORGANISM: Humicola hyalothermophila

<400> SEQUENCE: 2

Met Arg Ser Ser Pro Ile Leu Arg Lys Ala Val Ala Ala Leu Pro
1               5                   10                  15

Leu Gly Ala Tyr Ala Ala Ser Gly Asn Gly Gln Ser Thr Arg Tyr Trp
            20                  25                  30

Asp Cys Cys Lys Pro Ser Cys Ala Trp Pro Glu Lys Ala Ala Val Ser
            35                  40                  45

Gln Pro Val Tyr Ala Cys Asp Ala Asn Phe Gln Arg Ile Ser Asp Pro
    50                  55                  60

Leu Val Ser Ser Gly Cys Asp Gly Gly Gln Ala Phe Ser Cys Ala Asp
65                  70                  75                  80

His Ser Pro Trp Ala Leu Asn Asp Asn Leu Ser Tyr Gly Phe Ala Ala
                85                  90                  95

Thr Ala Leu Ala Gly Gly Thr Glu Ala Ser Trp Cys Cys Ala Cys Tyr
            100                 105                 110

Ala Leu Thr Phe Thr Ser Gly Pro Val Ala Gly Lys Thr Met Val Val
            115                 120                 125

Gln Ser Thr Ser Thr Gly Gly Asp Leu Gly Asn Asn His Phe Asp Leu
    130                 135                 140

Asn Ile Pro Gly Gly Gly Val Gly Leu Phe Asp Gly Cys Thr Pro Gln
145                 150                 155                 160

Phe Gly Gly Leu Pro Gly Ala Gln Tyr Gly Gly Ile Ser Ser Arg Ser
                165                 170                 175

Glu Cys Asp Ser Phe Pro Glu Pro Leu Lys Ala Gly Cys Tyr Trp Arg
            180                 185                 190

Phe Asp Trp Phe Gln Asn Ala Asp Asn Pro Ser Phe Thr Phe Glu Gln
            195                 200                 205

Val Gln Cys Pro Asp Glu Leu Val Ala Arg Thr Gly Cys Arg Arg Asn
    210                 215                 220

Asp Asp Gly Asn Phe Pro Val Phe Thr Pro Pro Ala Gly Gly Asn Asp
225                 230                 235                 240

Gly Glu Gln Pro Gly Asn Pro Gly Asp Cys Val Ala Gln Lys Trp Glu
                245                 250                 255

Gln Cys Gly Gly Ser Gly Phe Ser Gly Cys Thr Thr Cys Ala Ser Gly
            260                 265                 270

Ser Thr Cys Gln Val Val Asn Glu Trp Tyr Ser Gln Cys Val
    275                 280                 285

<210> SEQ ID NO 3
<211> LENGTH: 1057
<212> TYPE: DNA
<213> ORGANISM: Thielavia hyrcaniae
<220> FEATURE:
<221> NAME/KEY: exon
<222> LOCATION: (1)..(83)
<220> FEATURE:
<221> NAME/KEY: sig_peptide
<222> LOCATION: (1)..(63)
<220> FEATURE:
<221> NAME/KEY: exon
<222> LOCATION: (133)..(381)
<220> FEATURE:
<221> NAME/KEY: exon
<222> LOCATION: (438)..(1023)

<400> SEQUENCE: 3

```
atg cgc tcg act ccc gtt ctc cgc aca gcc atc gct gct gcc ctg ccc       48
Met Arg Ser Thr Pro Val Leu Arg Thr Ala Ile Ala Ala Ala Leu Pro
1               5                   10                  15 ctt gtg gca ttt gcc gct gat ggc aag tcg acc ag gtacgccgcc             93
Leu Val Ala Phe Ala Ala Asp Gly Lys Ser Thr Arg
            20                  25 tgaactcagt gttgccctca tcccgctgac accacccag g tac tgg gac tgc tgc     148
                                            Tyr Trp Asp Cys Cys
                                                    30 aag ccg tca tgc gcc tgg tcc ggc aag gct gcc gtg agc gcg ccc gtc      196
Lys Pro Ser Cys Ala Trp Ser Gly Lys Ala Ala Val Ser Ala Pro Val
        35                  40                  45 tac gcc tgc agc gcc aac ttc cag cgc ctc agc gac ccc aac gcc aag      244
Tyr Ala Cys Ser Ala Asn Phe Gln Arg Leu Ser Asp Pro Asn Ala Lys
50                  55                  60                  65 tct ggc tgc gat ggc ggc tcg gcc tac acc tgc gcc gac caa acg cct      292
Ser Gly Cys Asp Gly Gly Ser Ala Tyr Thr Cys Ala Asp Gln Thr Pro
                70                  75                  80 tgg gcc atc aat gac aac ctc tcg tac ggt ttc gcc gcc acc tcg atc      340
Trp Ala Ile Asn Asp Asn Leu Ser Tyr Gly Phe Ala Ala Thr Ser Ile
            85                  90                  95 tcg ggc ggt tcc gag gca tcg tgg tgc tgc gcc tgc tac ga               381
Ser Gly Gly Ser Glu Ala Ser Trp Cys Cys Ala Cys Tyr Glu
        100                 105                 110 gtgagtccca cgagtgagat cctcaaaaga acatgccaat cctaacctcg tcccag a      438 ctc acc ttt aac tcc ggt ccc gtg gcc ggc aag aag atg gtc gtc cag      486
Leu Thr Phe Asn Ser Gly Pro Val Ala Gly Lys Lys Met Val Val Gln
                115                 120                 125 tcc acc agc acc ggc ggc gac ctc ggc acc aac cac ttc gac ctc aac      534
Ser Thr Ser Thr Gly Gly Asp Leu Gly Thr Asn His Phe Asp Leu Asn
        130                 135                 140 atc ccc ggc ggc ggc gtc ggc ctc ttc gac ggc tgc aag aac cag ttc      582
Ile Pro Gly Gly Gly Val Gly Leu Phe Asp Gly Cys Lys Asn Gln Phe
145                 150                 155 ggc ggt ctc ccc ggc gcg cag tac ggc ggc atc tcg tcg cgc agc cag      630
Gly Gly Leu Pro Gly Ala Gln Tyr Gly Gly Ile Ser Ser Arg Ser Gln
160                 165                 170                 175 tgc gac tca ttc ccc gag gcc ctc aag ccc ggc tgc tac tgg cgc ttc      678
Cys Asp Ser Phe Pro Glu Ala Leu Lys Pro Gly Cys Tyr Trp Arg Phe
                180                 185                 190 gac tgg ttc cag aac gcc gac aac ccg acc ttc acc ttc cgc cag gtc      726
Asp Trp Phe Gln Asn Ala Asp Asn Pro Thr Phe Thr Phe Arg Gln Val
        195                 200                 205 cag tgc ccg tcc gag ctc gtc gcc cgc acc ggc tgc cgc cgc aac gac      774
Gln Cys Pro Ser Glu Leu Val Ala Arg Thr Gly Cys Arg Arg Asn Asp
210                 215                 220 gac tcc agc ttc ccc gtc ttc acc ccg ggc acc tcg ggc tcg tcc tcg      822
Asp Ser Ser Phe Pro Val Phe Thr Pro Gly Thr Ser Gly Ser Ser Ser
225                 230                 235 acc gcc aag ccc gct tcc tct tcg acc cgg gcc acg tcc acg aag acc      870
Thr Ala Lys Pro Ala Ser Ser Ser Thr Arg Ala Thr Ser Thr Lys Thr
240                 245                 250                 255 tcg gct cct gcg acc cag acg tcg tcg act gga ggc ggc tgc gtc gcg      918
Ser Ala Pro Ala Thr Gln Thr Ser Ser Thr Gly Gly Gly Cys Val Ala
                260                 265                 270 cag aag tgg gcg caa tgt ggt ggt agc gga ttt tct ggc tgc acc acc      966
Gln Lys Trp Ala Gln Cys Gly Gly Ser Gly Phe Ser Gly Cys Thr Thr
```

```
            275                 280                 285
tgc gct gcc ggg tcg acg tgc acg aag cag aac gac tac tac tcg cag    1014
Cys Ala Ala Gly Ser Thr Cys Thr Lys Gln Asn Asp Tyr Tyr Ser Gln
        290                 295                 300 tgc ctc taa atggcatgcg agtactcgtc tacccctttt ggcg                  1057
Cys Leu
    305

<210> SEQ ID NO 4
<211> LENGTH: 305
<212> TYPE: PRT
<213> ORGANISM: Thielavia hyrcaniae

<400> SEQUENCE: 4

Met Arg Ser Thr Pro Val Leu Arg Thr Ala Ile Ala Ala Ala Leu Pro
1               5                   10                  15

Leu Val Ala Phe Ala Ala Asp Gly Lys Ser Thr Arg Tyr Trp Asp Cys
            20                  25                  30

Cys Lys Pro Ser Cys Ala Trp Ser Gly Lys Ala Ala Val Ser Ala Pro
        35                  40                  45

Val Tyr Ala Cys Ser Ala Asn Phe Gln Arg Leu Ser Asp Pro Asn Ala
    50                  55                  60

Lys Ser Gly Cys Asp Gly Gly Ser Ala Tyr Thr Cys Ala Asp Gln Thr
65                  70                  75                  80

Pro Trp Ala Ile Asn Asp Asn Leu Ser Tyr Gly Phe Ala Ala Thr Ser
                85                  90                  95

Ile Ser Gly Gly Ser Glu Ala Ser Trp Cys Cys Ala Cys Tyr Glu Leu
            100                 105                 110

Thr Phe Asn Ser Gly Pro Val Ala Gly Lys Lys Met Val Val Gln Ser
        115                 120                 125

Thr Ser Thr Gly Gly Asp Leu Gly Thr Asn His Phe Asp Leu Asn Ile
    130                 135                 140

Pro Gly Gly Gly Val Gly Leu Phe Asp Gly Cys Lys Asn Gln Phe Gly
145                 150                 155                 160

Gly Leu Pro Gly Ala Gln Tyr Gly Gly Ile Ser Ser Arg Ser Gln Cys
                165                 170                 175

Asp Ser Phe Pro Glu Ala Leu Lys Pro Gly Cys Tyr Trp Arg Phe Asp
            180                 185                 190

Trp Phe Gln Asn Ala Asp Asn Pro Thr Phe Thr Phe Arg Gln Val Gln
        195                 200                 205

Cys Pro Ser Glu Leu Val Ala Arg Thr Gly Cys Arg Arg Asn Asp Asp
    210                 215                 220

Ser Ser Phe Pro Val Phe Thr Pro Gly Thr Ser Gly Ser Ser Ser Thr
225                 230                 235                 240

Ala Lys Pro Ala Ser Ser Ser Thr Arg Ala Thr Ser Thr Lys Thr Ser
                245                 250                 255

Ala Pro Ala Thr Gln Thr Ser Ser Thr Gly Gly Gly Cys Val Ala Gln
            260                 265                 270

Lys Trp Ala Gln Cys Gly Gly Ser Gly Phe Ser Gly Cys Thr Thr Cys
        275                 280                 285

Ala Ala Gly Ser Thr Cys Thr Lys Gln Asn Asp Tyr Tyr Ser Gln Cys
    290                 295                 300

Leu
305
```

```
<210> SEQ ID NO 5
<211> LENGTH: 874
<212> TYPE: DNA
<213> ORGANISM: Thielavia hyrcaniae
<220> FEATURE:
<221> NAME/KEY: exon
<222> LOCATION: (1)..(423)
<220> FEATURE:
<221> NAME/KEY: sig_peptide
<222> LOCATION: (1)..(54)
<220> FEATURE:
<221> NAME/KEY: exon
<222> LOCATION: (484)..(514)
<220> FEATURE:
<221> NAME/KEY: exon
<222> LOCATION: (570)..(696)
<220> FEATURE:
<221> NAME/KEY: exon
<222> LOCATION: (751)..(838)

<400> SEQUENCE: 5 atg cat ctc ccc ctg acc gcc gcc ctc gcc gtc ctc ccc gcc ctg gcg      48
Met His Leu Pro Leu Thr Ala Ala Leu Ala Val Leu Pro Ala Leu Ala
1               5                   10                  15 ctg ggc cag gcc acg ggc aag acg acg cgc tac tgg gac tgc tgc aag      96
Leu Gly Gln Ala Thr Gly Lys Thr Thr Arg Tyr Trp Asp Cys Cys Lys
            20                  25                  30 ccg agc tgc ggc tgg ccg ggc aag ggc acc agc ccg atc cgg acg tgc     144
Pro Ser Cys Gly Trp Pro Gly Lys Gly Thr Ser Pro Ile Arg Thr Cys
        35                  40                  45 gac aag aac gac aac gtg ctc aac gac ggc ggc aac acc aag tcc ggc     192
Asp Lys Asn Asp Asn Val Leu Asn Asp Gly Gly Asn Thr Lys Ser Gly
 50                  55                  60 tgc gac aac ggc ggc ggc gcc tac atg tgc tcc aac cag agc ccc tgg     240
Cys Asp Asn Gly Gly Gly Ala Tyr Met Cys Ser Asn Gln Ser Pro Trp
65                  70                  75                  80 gcc gtc aac gac tcg ctc gcc tac ggc tgg gcg gcc gtc aac atc gcc     288
Ala Val Asn Asp Ser Leu Ala Tyr Gly Trp Ala Ala Val Asn Ile Ala
                85                  90                  95 ggc agc tcc gag tcg cag tgg tgc tgt gcc tgt tat gag ctg acc ttc     336
Gly Ser Ser Glu Ser Gln Trp Cys Cys Ala Cys Tyr Glu Leu Thr Phe
            100                 105                 110 acg agc ggg ccg gtg cag ggc aag aag atg att gtg cag gcg tcg aat     384
Thr Ser Gly Pro Val Gln Gly Lys Lys Met Ile Val Gln Ala Ser Asn
        115                 120                 125 acg ggc ggg gat ttg ggg aat aat cat ttt gac ctc gcc gtgcgtttcc     433
Thr Gly Gly Asp Leu Gly Asn Asn His Phe Asp Leu Ala
    130                 135                 140 catgctacct cgagggtaag gctcttaact gacgagatat acctcaacag atc ccc     489
                                                      Ile Pro ggc ggt ggt gtt ggc atc ttc aac g gtaagccctt tttcccttct              534
Gly Gly Gly Val Gly Ile Phe Asn
145                 150 tctcgaaggt aaacatgaat actgacgtag aacag cc tgc acc aac cag tac       586
                                      Ala Cys Thr Asn Gln Tyr
                                                        155 ggc gcc ccc tcc aac ggc tgg ggc gac cgc tac ggc ggc atc cac tcc     634
Gly Ala Pro Ser Asn Gly Trp Gly Asp Arg Tyr Gly Gly Ile His Ser
            160                 165                 170 cag agc gag tgt aac agc ttt ccc gag aag ctc aag gcc ggc tgc aac     682
Gln Ser Glu Cys Asn Ser Phe Pro Glu Lys Leu Lys Ala Gly Cys Asn
        175                 180                 185 tgg cgc ttt gac tg gtgcgtaccg tgatgactgc tgaaagtgag aaacccaact     736
Trp Arg Phe Asp Trp
```

```
                                                                       190
gacaacctcc acag g ttc aag aat gcc gac aac ccg tcg gtt acc ttc aag      787
              Phe Lys Asn Ala Asp Asn Pro Ser Val Thr Phe Lys
                 195                 200                 205 cag gtc tcc tgc ccg gcc gag atc act gcc aag agc ggt tgt ggt cgc        835
Gln Val Ser Cys Pro Ala Glu Ile Thr Ala Lys Ser Gly Cys Gly Arg
        210                 215                 220 taa ggaggggag gaaagtggct gtatgcgatg gtgaat                             874
```

<210> SEQ ID NO 6
<211> LENGTH: 222
<212> TYPE: PRT
<213> ORGANISM: Thielavia hyrcaniae

<400> SEQUENCE: 6

Met His Leu Pro Leu Thr Ala Ala Leu Ala Val Leu Pro Ala Leu Ala
1               5                   10                  15

Leu Gly Gln Ala Thr Gly Lys Thr Thr Arg Tyr Trp Asp Cys Cys Lys
            20                  25                  30

Pro Ser Cys Gly Trp Pro Gly Lys Gly Thr Ser Pro Ile Arg Thr Cys
        35                  40                  45

Asp Lys Asn Asp Asn Val Leu Asn Asp Gly Gly Asn Thr Lys Ser Gly
    50                  55                  60

Cys Asp Asn Gly Gly Gly Ala Tyr Met Cys Ser Asn Gln Ser Pro Trp
65                  70                  75                  80

Ala Val Asn Asp Ser Leu Ala Tyr Gly Trp Ala Ala Val Asn Ile Ala
                85                  90                  95

Gly Ser Ser Glu Ser Gln Trp Cys Cys Ala Cys Tyr Glu Leu Thr Phe
            100                 105                 110

Thr Ser Gly Pro Val Gln Gly Lys Lys Met Ile Val Gln Ala Ser Asn
        115                 120                 125

Thr Gly Gly Asp Leu Gly Asn Asn His Phe Asp Leu Ala Ile Pro Gly
    130                 135                 140

Gly Gly Val Gly Ile Phe Asn Ala Cys Thr Asn Gln Tyr Gly Ala Pro
145                 150                 155                 160

Ser Asn Gly Trp Gly Asp Arg Tyr Gly Gly Ile His Ser Gln Ser Glu
                165                 170                 175

Cys Asn Ser Phe Pro Glu Lys Leu Lys Ala Gly Cys Asn Trp Arg Phe
            180                 185                 190

Asp Trp Phe Lys Asn Ala Asp Asn Pro Ser Val Thr Phe Lys Gln Val
        195                 200                 205

Ser Cys Pro Ala Glu Ile Thr Ala Lys Ser Gly Cys Gly Arg
    210                 215                 220

<210> SEQ ID NO 7
<211> LENGTH: 305
<212> TYPE: PRT
<213> ORGANISM: Artificial Sequence
<220> FEATURE:
<223> OTHER INFORMATION: Synthetic construct

<400> SEQUENCE: 7

Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro

```
                35                  40                  45
Val Phe Ser Cys Asn Ala Asn Phe Gln Arg Ile Thr Asp Phe Asp Ala
 50                  55                  60

Lys Ser Gly Cys Glu Pro Gly Val Ala Tyr Ser Cys Ala Asp Gln
 65                  70                  75                  80

Thr Pro Trp Ala Val Asn Asp Phe Ala Leu Gly Phe Ala Ala Thr
                 85                  90                  95

Ser Ile Ala Gly Ser Asn Glu Ala Gly Trp Cys Cys Ala Cys Tyr Glu
                100                 105                 110

Leu Thr Phe Thr Ser Gly Pro Val Ala Gly Lys Lys Met Val Val Gln
                115                 120                 125

Ser Thr Ser Thr Gly Gly Asp Leu Gly Ser Asn His Phe Asp Leu Asn
130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
                180                 185                 190

Asp Trp Phe Lys Asn Ala Asp Asn Pro Ser Phe Ser Phe Arg Gln Val
                195                 200                 205

Gln Cys Pro Ala Glu Leu Val Ala Arg Thr Gly Cys Arg Arg Asn Asp
 210                 215                 220

Asp Gly Asn Phe Pro Ala Val Gln Ile Pro Ser Ser Thr Ser Ser
225                 230                 235                 240

Pro Val Asn Gln Pro Thr Ser Thr Ser Thr Thr Ser Thr Ser Thr Thr
                245                 250                 255

Ser Ser Pro Pro Val Gln Pro Thr Thr Pro Ser Gly Cys Thr Ala Glu
                260                 265                 270

Arg Trp Ala Gln Cys Gly Gly Asn Gly Trp Ser Gly Cys Thr Thr Cys
                275                 280                 285

Val Ala Gly Ser Thr Cys Thr Lys Ile Asn Asp Trp Tyr His Gln Cys
 290                 295                 300

Leu
305

<210> SEQ ID NO 8
<211> LENGTH: 43
<212> TYPE: DNA
<213> ORGANISM: Artificial Sequence
<220> FEATURE:
<223> OTHER INFORMATION: synthetic construct

<400> SEQUENCE: 8
acacaactgg ggatccacca tgcgttcttc tcctatcctt cgc                       43

<210> SEQ ID NO 9
<211> LENGTH: 38
<212> TYPE: DNA
<213> ORGANISM: Artificial Sequence
<220> FEATURE:
<223> OTHER INFORMATION: synthetic construct

<400> SEQUENCE: 9
gtcaccctct agatctgcca tctgacctca gcagaaca                             38

<210> SEQ ID NO 10
```

```
<211> LENGTH: 38
<212> TYPE: DNA
<213> ORGANISM: Artificial Sequence
<220> FEATURE:
<223> OTHER INFORMATION: synthetic construct

<400> SEQUENCE: 10
acacaactgg ggatccacca tgcgctcgac tcccgttc                                38

<210> SEQ ID NO 11
<211> LENGTH: 41
<212> TYPE: DNA
<213> ORGANISM: Artificial Sequence
<220> FEATURE:
<223> OTHER INFORMATION: synthetic construct

<400> SEQUENCE: 11
gtcaccctct agatctcgcc aaaaggggta gacgagtact c                            41

<210> SEQ ID NO 12
<211> LENGTH: 34
<212> TYPE: DNA
<213> ORGANISM: Artificial Sequence
<220> FEATURE:
<223> OTHER INFORMATION: synthetic construct

<400> SEQUENCE: 12
acacaactgg ggatccacca tgcatctccc cctg                                    34

<210> SEQ ID NO 13
<211> LENGTH: 38
<212> TYPE: DNA
<213> ORGANISM: Artificial Sequence
<220> FEATURE:
<223> OTHER INFORMATION: synthetic construct

<400> SEQUENCE: 13
gtcaccctct agatctattc accatcgcat acagccac                                38
```

POLYPEPTIDES HAVING ENDOGLUCANASE ACTIVITY AND POLYNUCLEOTIDES ENCODING SAME

CROSS-REFERENCE TO RELATED APPLICATIONS

This application is a 35 U.S.C. 371 national application of PCT/CN2013/090355 filed Dec. 24, 2013, which claims priority or the benefit under 35 U.S.C. 119 of international application nos. PCT/CN2012/087339, PCT/CN2012/087336 and PCT/CN2012/087345, each filed Dec. 24, 2012, and U.S. provisional application Nos. 61/760,228, 61/760,230 and 61/760,226, each filed Feb. 4, 2013. The content of each application is fully incorporated herein by reference.

REFERENCE TO A SEQUENCE LISTING

This application contains a Sequence Listing in computer readable form, which is incorporated herein by reference.

REFERENCE TO A DEPOSIT OF BIOLOGICAL MATERIAL

This application contains a reference to a deposit of biological material, which deposit is incorporated herein by reference.

BACKGROUND OF THE INVENTION

Field of the Invention

The present invention relates to polypeptides having endoglucanase activity, catalytic domains, and carbohydrate binding module, and polynucleotides encoding the polypeptides, catalytic domains, and carbohydrate binding domains. The invention also relates to nucleic acid constructs, vectors, and host cells comprising the polynucleotides as well as methods of producing and using the polypeptides, catalytic domains, and carbohydrate binding domains. The present invention also relates to the method for manufacturing textile, by treating textile with an isolated polypeptide having endoglucanase activity, especially in biostoning and biopolishing process.

Description of the Related Art

Cellulases or cellulytic enzymes are enzymes involved in hydrolyses of cellulose. It is known that there are three major types of cellulase enzymes involved, namely endoglucanase, cellobiohydrolase, and beta-glucosidase.

There is a wide spectrum of industrial applications of cellulases. In the textile industry, cellulases are used in denim finishing to create a fashionable stone washed appearance on denim cloths using a biostoning process. Cellulases are also used, for instance, to clean fuzz and prevent formation of pills on the surface of cotton garments using a biopolishing process.

WO 96/29397 discloses enzyme preparations with performance in industrial applications such as laundry composition, for biopolishing of newly manufactured textiles, for providing an abraded look of cellulosic fabric or garment, and for treatment of paper pulp.

WO 2010/076388 discloses fungal endoglucanases with substantial performance at low temperatures; the endoglucanases are used for treating cellulosic material, especially in textile industry, e.g. in biofinishing or biostoning.

A Glycoside hydrolase family 45 protein from *Thielavia terrestris* is disclosed as UNIPROT: G2QVH7. A polypeptide from *Thielavia terrestris* having endoglucanase activity is disclosed as GENESEQP: AZX33567.

An endo-beta-D-1,4-glucanase from *Staphylotrichum coccosporum* is disclosed as UNIPROT: B5BNY1. A polypeptide from *Staphylotrichum coccosporum* having endoglucanase activity is disclosed as GENESEQP: AEA35116.

An endoglucanase from *Thielavia terrestris* is disclosed as UNIPROT: G2R3B9. A polypeptide from *Chrysosporium lucknowense* having endoglucanase activity is disclosed as GENESEQP: ATS95010. There are continued needs in the art for new endoglucanases and methods for obtaining a cellulosic textile fabric with good abrasion effect, and/or reduced tendency to pilling formation in the biopolishing process, especially at low temperature.

The present invention aims to meet these needs and provides polypeptides having endoglucanase activity and polynucleotides encoding the polypeptides.

SUMMARY OF THE INVENTION

The present invention relates to isolated polypeptides having endoglucanase activity selected from the group consisting of:

(a) a polypeptide having at least 80% sequence identity to the mature polypeptide of SEQ ID NO: 2, or a polypeptide having at least 85% sequence identity to the mature polypeptide of SEQ ID NO: 4; a polypeptide having at least 85% sequence identity to the mature polypeptide of SEQ ID NO: 6;

(b) a polypeptide encoded by a polynucleotide that hybridizes under medium, medium-high, high, or very high stringency conditions with (i) the mature polypeptide coding sequence of SEQ ID NO: 1 or SEQ ID NO: 3 or SEQ ID NO: 5, (II) the cDNA sequence thereof, or (iii) the full-length complement of (i) or (ii);

(c) a polypeptide encoded by a polynucleotide having at least 80% sequence identity to the mature polypeptide coding sequence of SEQ ID NO: 1, or encoded by a polynucleotide having at least 85% sequence identity to the mature polypeptide coding sequence of SEQ ID NO: 3, or encoded by a polynucleotide having at least 85% sequence identity to the mature polypeptide coding sequence of SEQ ID NO: 5, or the cDNA sequence thereof;

(d) a variant of the mature polypeptide of SEQ ID NO: 2 or SEQ ID NO: 4 or SEQ ID NO: 6 comprising a substitution, deletion, and/or insertion at one or more (e.g., several) positions; and (e) a fragment of the polypeptide of (a), (b), (c), or (d) that has endoglucanase activity.

The present invention also relates to isolated polypeptides comprising a catalytic domain selected from the group consisting of:

(a) a catalytic domain having at least 85% sequence identity to amino acids 22 to 237 of SEQ ID NO: 2, or at least 90% sequence identity to amino acids 22 to 223 of SEQ ID NO: 4, or at least 85% sequence identity to amino acids 21 to 222 of SEQ ID NO: 6;

(b) a catalytic domain encoded by a polynucleotide that hybridizes under medium, medium-high, high, or very high stringency conditions with (i) nucleotides 64 to 838 of SEQ ID NO: 1, or nucleotides 64 to 774 of SEQ ID NO: 3, or nucleotides 61 to 835 of SEQ ID NO: 5, (ii) the cDNA sequence thereof, or (iii) the full-length complement of (i) or (ii);

(c) a catalytic domain encoded by a polynucleotide having at least 85% sequence identity to nucleotides 64 to 838 of SEQ ID NO: 1, or at least 90% sequence identity to nucleotides 64 to 774 of SEQ ID NO: 3, or at least 85% sequence identity to nucleotides 61 to 835 of SEQ ID NO: 5 or the cDNA sequence thereof;

(d) a variant of amino acids 22 to 237 of SEQ ID NO: 2, or a variant of amino acids 22 to 223 of SEQ ID NO: 4, or at least 85% sequence identity to nucleotides 21 to 222 of SEQ ID NO: 6 comprising a substitution, deletion, and/or insertion at one or more (e.g., several) positions; and (e) a fragment of the catalytic domain of (a), (b), (c), or (d) that has endoglucanase activity.

The present invention also relates to isolated polypeptides comprising a carbohydrate binding module selected from the group consisting of:

(a) a carbohydrate binding module having at least 80% sequence identity to amino acids 250 to 286 of SEQ ID NO: 2, or at least 85% sequence identity to amino acids 268 to 305 of SEQ ID NO: 4;

(b) a carbohydrate binding module encoded by a polynucleotide that hybridizes under medium, medium-high, high, or very high stringency conditions with (i) nucleotides 875 to 985 of SEQ ID NO: 1 or nucleotides 907 to 1020 of SEQ ID NO: 3, (ii) the cDNA sequence thereof, or (iii) the full-length complement of (i) or (ii);

(c) a carbohydrate binding module encoded by a polynucleotide having at least 80% sequence identity to nucleotides 875 to 985 of SEQ ID NO: 1, or at least 85% sequence identity to nucleotides 907 to 1020 of SEQ ID NO: 3 or the cDNA sequence thereof;

(d) a variant of amino acids 250 to 286 of SEQ ID NO: 2 or a variant of amino acids 268 to 305 of SEQ ID NO: 4 comprising a substitution, deletion, and/or insertion at one or more (e.g., several) positions; and (e) a fragment of the carbohydrate binding module of (a), (b), (c), or (d) that has binding activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to a polynucleotide encoding a signal peptide comprising or consisting of amino acids 1 to 21 of SEQ ID NO: 2 or amino acids 1 to 21 of SEQ ID NO: 4 or amino acids 1 to 18 of SEQ ID NO: 6; nucleic acid constructs, expression vectors, and recombinant host cells comprising the polynucleotides; and methods of producing a protein.

The present invention also relates to the method for manufacturing textile, by treating textile with an isolated polypeptide having endoglucanase activity, especially in biostoning and biopolishing process.

In some embodiments, the method may be applied to a biopolishing process. In some embodiment, the method is conducted with a dyestuff in one bath. In some embodiment, the method is conducted with catalase in one bath.

In some embodiments, the method for manufacturing textile is provided. In some embodiments, the textile is manufactured from fabric to garment.

In some embodiments, the textile is cellulose-containing or cellulosic textile.

The advantage of the present invention is that the method can be conducted in low temperature, so as to save energy in textile manufacturing process. The method of the present invention may further show good compatibility with dyeing step.

DEFINITIONS

Endoglucanase

Figure 1:
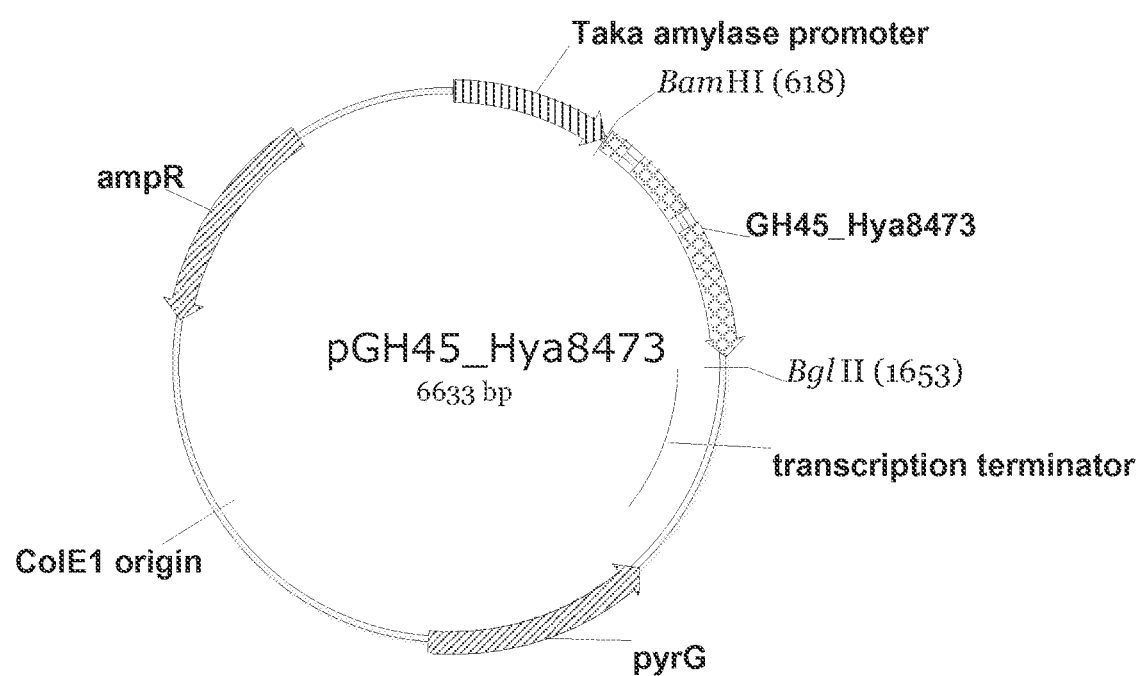
FIG. 1: DNA map of vector pGH45_Hya8473 for expressing the *Humicola hyalothermophila* GH45 endoglucanase gene.

The term "endoglucanase" means an endo-1,4-(1,3;1,4)-beta-D-glucan 4-glucanohydrolase (E.C. 3.2.1.4), which catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, Biotechnology Advances 24: 452-481). Endoglucanase activity can also be determined using carboxymethyl cellulose (CMC) as substrate according to the procedure of part VI in page 264 of Ghose, 1987, Pure and Appl. Chem. 59: 257-268.

For purposes of the present invention, endoglucanase activity is determined according to the procedure described in the Examples. In one aspect, the polypeptides of the present invention have at least 50%, at least 60%, at least 70%, at least 80%, at least 90%, at least 95%, or at least 100% of the endoglucanase activity of the mature polypeptide of SEQ ID NO: 2 or SEQ ID NO: 4 or SEQ ID NO: 6.

Typically, the endoglucanase has at least two functional domains, a carbohydrate binding module (CBM) and a catalytic module. The catalytic module is defined as an amino acid sequence that is capable of enzymatically cleaving cellulose, e.g. has endoglucanase activity. The catalytic module is not considered to be a carbohydrate-binding module. A "linker sequence" connects the two functional modules.

Carbohydrate-Binding Module:

The term "carbohydrate-binding module" (CBM) is defined as an amino acid sequence that binds to a substrate. CBMs are for example described in Boraston et al., 2004, Biochem, J. 382: 769-781 and in Tomme et al., John N. Saddler and Michael H. Penner (Eds.), ACS Symposium Series, No, 618, 1995. It is believed that the CBM binding to the substrate which increases the efficacy of the catalytic active part of the enzyme.

The term CBM is now in general use; however, the term "cellulose-binding domain" (CBD) is used to describe the subset of CBM that bind specifically to cellulose substrate. In context, CBM or CBD of the polypeptide having endoglucanase activity could be used interchangeably.

Family 45 or Family GH45 or CEL45:

The term "Family 45" or "Family GH45" or "CEL45" is defined herein as a polypeptide falling into the glycoside hydrolase Family 45 according to Henrissat B., 1991, A classification of glycosyl hydrolases based on amino-acid sequence similarities, Biochem. J. 280: 309-316, and Henrissat and Bairoch, 1996, Updating the sequence-based classification of glycosyl hydrolases, Biochem. J. 316: 695-696. Carbohydrate binding modules are often associated with catalytic modules encoding enzymes such as glycosyl hydrolases. Guillén D, Sánchez S, Rodriguez-Sanoja R. Carbohydrate-binding domains: multiplicity of biological roles. Applied Microbiology & Biotechnology February 2010; 85(5):1241. Available from: EDS Foundation Index, Ipswich, Mass.

Allelic Variant:

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic Domain:

The term "catalytic domain" means the region of an enzyme containing the catalytic machinery of the enzyme.

cDNA:

The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding Sequence:

The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control Sequences:

The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression:

The term "expression" includes any step involved in the production of a polypeptide including, but not limited to, transcription, post-transcriptional modification, translation, post-translational modification, and secretion.

Expression Vector:

The term "expression vector" means a linear or circular DNA molecule that comprises a polynucleotide encoding a polypeptide and is operably linked to control sequences that provide for its expression.

Fragment:

The term "fragment" means a polypeptide or a catalytic domain or carbohydrate binding module having one or more (e.g., several) amino acids absent from the amino and/or carboxyl terminus of a mature polypeptide or domain; wherein the fragment has endoglucanase or carbohydrate binding activity. In one aspect, a fragment contains at least 85%, 90%, or 95% of the number of amino acids of the mature polypeptide of SEQ ID NO: 2 or SEQ ID NO: 4 or SEQ ID NO: 6.

High Stringency Conditions:

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65'C.

Host Cell:

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated:

The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature Polypeptide:

The term "mature polypeptide" means a polypeptide in its final form following translation and any post-translational modifications, such as N-terminal processing, C-terminal truncation, glycosylation, phosphorylation, etc. In one aspect. the mature polypeptide is amino acids 22 to 286 of SEQ ID NO: 2. amino acid 22 to 305 of SEQ ID NO: 4 and amino acids 19 to 222 of SEQ ID NO: 6 based on SignalP 3.0 program (Bendtsen et al., 2004, *J. Mol. Biol.* 340: 783-795) that predicts amino acids 1 to 21 of SEQ ID NO: 2 are a signal peptide. It is further confirmed by the N-terminal sequencing, showing mature peptide begins with ASGNGQS (amino acids 22 to 28 of SEQ ID NO: 2), which is consistent with the prediction that amino acids 1 to 21 of SEQ ID NO: 2 are a signal peptide. It is further confirmed by the N-terminal sequencing, showing mature peptide begins with ADGKSTR (amino acids 22 to 28 of SEQ ID NO: 4), which is consistent with the prediction that amino acids 1 to 21 of SEQ ID NO: 4 are a signal peptide. It is further confirmed by the N-terminal sequencing, showing mature peptide begins with QATGKTT (amino acids 19 to 25 of SEQ ID NO: 6), which is consistent with the prediction that amino acids 1 to 18 of SEQ ID NO: 6 are a signal peptide.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide. In one aspect, a mature polypeptides contains up to 105%, 110%, and 115% of the number of amino acids of the mature polypeptide of SEQ ID NO: 2 or SEQ ID NO: 4 or SEQ ID NO: 6.

Mature Polypeptide Coding Sequence:

The term "mature polypeptide coding sequence" means a polynucleotide that encodes a mature polypeptide having endoglucanase activity. In one aspect, the mature polypeptide coding sequence is nucleotides 64 to 985 of SEQ ID NO: 1 or the cDNA sequence thereof based on the SignalP 3.0 program (Bendtsen et al., 2004, supra) that predicts nucleotides 1 to 63 of SEQ ID NO: 1 encode a signal peptide. In another aspect, the mature polypeptide coding sequence is nucleotides 64 to 1020 of SEQ ID NO: 3 or the cDNA sequence thereof based on the SignalP 3.0 program (Bendtsen et al., 2004, supra) that predicts nucleotides 1 to 63 of SEQ ID NO: 3 encode a signal peptide. In another aspect, the mature polypeptide coding sequence is nucleotides 55 to 835 of SEQ ID NO: 5 or the cDNA sequence thereof based on the SignalP 3.0 program (Bendtsen et al., 2004, supra) that predicts nucleotides 1 to 54 of SEQ ID NO: 5 encode a signal peptide.

Medium Stringency Conditions:

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

Medium-High Stringency Conditions:

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

Nucleic Acid Construct:

The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably Linked:

The term "operably linked" means a configuration in which a control sequence is placed at an appropriate position relative to the coding sequence of a polynucleotide such that the control sequence directs expression of the coding sequence.

Sequence Identity:

The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of
Alignment−Total Number of Gaps in Alignment)

Subsequence:

The term "subsequence" means a polynucleotide having one or more (e.g., several) nucleotides absent from the 5' and/or 3' end of a mature polypeptide coding sequence; wherein the subsequence encodes a fragment having endoglucanase activity.

Variant:

The term "variant" means a polypeptide having endoglucanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding one or more (e.g., several) amino acids, e.g., 1-5 amino acids, adjacent to the amino acid occupying a position.

Very High Stringency Conditions:

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Textile:

The term "textiles" used herein is meant to include fibers, yarns, fabrics and garments.

Fabric can be constructed from fibers by weaving, knitting or non-woven operations. Weaving and knitting require yarn as the input whereas the non-woven fabric is the result of random bonding of fibers (paper can be thought of as non-woven). In the present context, the term "fabric" is also intended to include fibers and other types of processed fabrics.

According to the invention, the method of the invention may be applied to any textile known in the art (woven, knitted, or non-woven). In particular the process of the present invention may be applied to cellulose-containing or cellulosic textile, such as cotton, viscose, rayon, ramie, linen, lyocell (e.g., Tencel, produced by Courtaulds Fibers), or mixtures thereof, or mixtures of any of these fibers together with synthetic fibres (e.g., polyester, polyamid, nylon) or other natural fibers such as wool and silk, such as viscose/cotton blends, lyocell/cotton blends, viscose/wool blends, lyocell/wool blends, cotton/wool blends; flax (linen), ramie and other fabrics based on cellulose fibers, including all blends of cellulosic fibers with other fibers such as wool, polyimide, acrylic and polyester fibers, e.g., viscose/cotton/polyester blends, wool/cotton/polyester blends, flax/cotton blends etc.

DETAILED DESCRIPTION OF THE INVENTION

Polypeptides Having Endoglucanase Activity

In an embodiment, the present invention relates to isolated polypeptides having a sequence identity to the mature polypeptide of SEQ ID NO: 2 of at least 80%, e.g., at least 80%, at least 85%, at least 90%, at least 91%, at least 92%, at least 93%, at least 94%, at least 95%, at least 96%, at least 97%, at least 98%, at least 99%, or 100%, which have endoglucanase activity. In an embodiment, the present invention relates to isolated polypeptides having a sequence identity to the mature polypeptide of SEQ ID NO: 4 of at least 85%, e.g., at least 85%, at least 90%, at least 91%, at least 92%, at least 93%, at least 94%, at least 95%, at least 96%, at least 97%, at least 98%, at least 99%, or 100%, which have endoglucanase activity. In an embodiment, the present invention relates to isolated polypeptides having a sequence identity to the mature polypeptide of SEQ ID NO: 6 of at least 85%, e.g., at least 85%, at least 90%, at least 91%, at least 92%, at least 93%, at least 94%, at least 95%, at least 96%, at least 97%, at least 98%, at least 99%, or 100%, which have endoglucanase activity. In one aspect, the polypeptides differ by up to 10 amino acids, e.g., 1, 2, 3, 4, 5, 6, 7, 8, 9, or 10, from the mature polypeptide of SEQ ID NO: 2 or SEQ ID NO: 4 or SEQ ID NO: 6.

A polypeptide of the present invention preferably comprises or consists of the amino acid sequence of SEQ ID NO: 2 or SEQ ID NO: 4 or SEQ ID NO: 6 or an allelic variant thereof; or is a fragment thereof having endoglucanase activity. In another aspect, the polypeptide comprises or consists of the mature polypeptide of SEQ ID NO: 2 or SEQ ID NO: 4 or SEQ ID NO: 6. In another aspect, the polypeptide comprises or consists of amino acids 22 to 286 of SEQ ID NO: 2, amino acids 22 to 305 of SEQ ID NO: 4 or amino acid 19 to 222 of SEQ ID NO: 6. In another embodiment, the present invention relates to an isolated polypeptide having endoglucanase activity encoded by a polynucleotide that hybridizes under medium stringency conditions, medium-high stringency conditions, high stringency conditions, or very high stringency conditions with (i) the mature polypeptide coding sequence of SEQ ID NO: 1 or SEQ ID NO: 3 or SEQ ID NO: 5, (ii) the cDNA sequence thereof, or (iii) the full-length complement of (i) or (ii) (Sambrook et al., 1989, *Molecular Cloning, A Laboratory Manual,* 2d edition, Cold Spring Harbor, N.Y.).

The polynucleotide of SEQ ID NO: 1 or SEQ ID NO: 3 or SEQ ID NO: 5 or a subsequence thereof, as well as the polypeptide of SEQ ID NO: 2 or SEQ ID NO: 4 or SEQ ID NO: 6 or a fragment thereof, may be used to design nucleic acid probes to identify and done DNA encoding polypeptides having endoglucanase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at east 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having endoglucanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or SEQ ID NO: 3 or SEQ ID NO: 5 or a subsequence thereof, the carrier material is used in a Southern blot.

For purposes of the present invention, hybridization indicates that the polynucleotide hybridizes to a labeled nucleic acid probe corresponding to (i) SEQ ID NO: 1 or SEQ ID NO: 3 or SEQ ID NO: 5; (ii) the mature polypeptide coding sequence of SEQ ID NO: 1 or SEQ ID NO: 3 or SEQ ID NO: 5; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2 or SEQ ID NO: 4 or SEQ ID NO: 6; the mature polypeptide thereof; or a fragment thereof. In another aspect, the nucleic acid probe is SEQ ID NO: 1 or SEQ ID NO: 3 or SEQ ID NO: 5 or the cDNA sequence thereof.

In another embodiment, the present invention relates to an isolated polypeptide having endoglucanase activity encoded by a polynucleotide having a sequence identity to the mature polypeptide coding sequence of SEQ ID NO: 1 or SEQ ID NO: 3 or SEQ ID NO: 5 or the cDNA sequence thereof of at least 80%, e.g., at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2 or SEQ ID NO: 4 or SEQ ID NO: 6 comprising a substitution, deletion, and/or insertion at one or more (e.g., several) positions. In an embodiment, the number of amino acid substitutions, deletions and/or insertions introduced into the mature polypeptide of SEQ ID NO: 2 or SEQ ID NO: 4 or SEQ ID NO: 6 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for endoglucanase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et 1994, Science 266: 776-779).

A fusion polypeptide can further comprise a cleavage site between the two polypeptides. Upon secretion of the fusion protein, the site is cleaved releasing the two polypeptides, Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et. al., 1995, Biotechnology 13: 982-987; Carter et al., 1989, Proteins: Structure, Function, and Genetics 6: 240-248; and Stevens, 2003, Drug Discovery World 4: 35-48.

Sources of Polypeptides Having Endoglucanase Activity

A polypeptide having endoglucanase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. For example, the polypeptide may be a *Humicola* polypeptide.

In another aspect, the polypeptide is a *Humicola hyalothermophila*, *Humicola grisea*, *Humicola lanuginosa* or *Humicola insolens* polypeptide.

In another aspect, the polypeptide is a *Thielavia* polypeptide, for example *Thielavia hyrcaniae*, *Thielavia appendiculata*, *Thielavia arenaria*, *Thielavia australiensis*, *Thielavia basicola*, *Thielavia coactilis*, *Thielavia dacrydioides*, *Thielavia fragilis*, *Thielavia heterothallica*, *Thielavia hyalocarpa*, *Thielavia hyrcaniae*, *Thielavia inaequalis*, *Thielavia intermedia*, *Thielavia kuwaitensis*, *Thielavia microspora*, *Thielavia minuta*, *Thielavia ovispora*, *Thielavia pallidospora*, *Thielavia peruviana*, *Thielavia subthermophila*, *Thielavia terrestris*, *Thielavia terricola*, *Thielavia tortuosa* or *Thielavia wareingii* polypeptide. It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

In one embodiment, the present invention also relates to catalytic domains having a sequence identity to amino acids 22 to 237 of SEQ ID NO: 2 of at least 85%, e.g., at least 90%, at least 95%, at least 96%, at least 97%, at least 98%, at least 99%, or 100%. In one embodiment, the present invention also relates to catalytic domains having a sequence identity to amino acids 22 to 223 of SEQ ID NO: 4 of at least 90%, e.g., at least 95%, at least 96%, at least 97%, at least 98%, at least 99%, or 100%. In one embodiment, the present invention also relates to catalytic domains having a sequence identity to amino acids 21 to 222 of SEQ ID NO: 6 of at least 85%, e.g., at least 85%, at least 90%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 22 to 237 of SEQ ID NO: 2, amino acids 22 to 223 of SEQ ID NO: 4 or amino acids 21 to 222 of SEQ ID NO: 6.

The catalytic domain preferably comprises or consists of amino acids 22 to 237 of SEQ ID NO: 2, amino acids 22 to 223 of SEQ ID NO: 4 or amino acids 21 to 222 of SEQ ID NO: 6 or an allelic variant thereof; or is a fragment thereof having endoglucanase activity.

In another embodiment, the present invention also relates to catalytic domains encoded by polynucleotides that hybridize under medium stringency conditions, medium-high stringency conditions, high stringency conditions, or very high stringency conditions (as defined above) with (i) the nucleotides 64 to 838 of SEQ ID NO: 1, the nucleotides 64 to 774 of SEQ ID NO: 3 or the nucleotides 61 to 835 of SEQ ID NO: 5, (ii) the cDNA sequence thereof, or (iii) the full-length complement of (i) or (ii) (Sambrook et al., 1989, supra).

In another embodiment, the present invention also relates to catalytic domains encoded by polynucleotides having a sequence identity to nucleotides 64 to 838 of SEQ ID NO: 1, the nucleotides 64 to 774 of SEQ ID NO: 3 or the nucleotides 61 to 835 of SEQ ID NO: 5 or the cDNA sequence thereof at least 85%, e.g., at least 90%, at least 91%, at least 92%, at least 93%, at least 94%, at least 95%, at least 96%, at least 97%, at least 98%, at least 99%, or 100%.

The polynucleotide encoding the catalytic domain preferably comprises or consists of nucleotides 64 to 838 of SEQ ID NO: 1, the nucleotides 64 to 774 of SEQ ID NO: 3 or the nucleotides 61 to 835 of SEQ ID NO: 5 or is the sequence contained in pGH45_Hya8473 or pGH45_Thihy3331 or pGH45_Thihy0507.

In another embodiment, the present invention also relates to catalytic domain variants of amino acids 22 to 237 of SEQ ID NO: 2 or amino acids 22 to 223 of SEQ ID NO: 4 or amino acids 21 to 222 of SEQ ID NO: 6 comprising a substitution, deletion, and/or insertion at one or more (e.g., several) positions. In one aspect, the number of amino acid substitutions, deletions and/or insertions introduced into the sequence of amino acids 22 to 237 of SEQ ID NO: 2 amino acids 22 to 223 of SEQ ID NO: 4 or amino acids 21 to 222 of SEQ ID NO: 6 is up to 10, e.g., 1, 2, 3, 4, 5, 6, 8, 9, or 10.

Binding Domains

In one embodiment, the present invention also relates to carbohydrate binding modules having a sequence identity to amino acids 250 to 286 of SEQ ID NO: 2 of at least 80%, e.g., at least 85%, at least 90%, at least 91%, at least 92%, at least 93%, at least 94%, at least 95%, at least 96%, at least 97%, at least 98%, at least 99%, or 100%. In one embodiment, the present invention also relates to carbohydrate binding modules having a sequence identity to amino acids 268 to 305 of SEQ ID NO: 4 of at least 85%, e.g., at least 90%, at least 91%, at least 92%, at least 93%, at least 94%, at least 95%, at least 96%, at least 97%, at least 98%, at least 99%, or 100%. In one aspect, the carbohydrate binding modules comprise amino acid sequences that differ by up to 10 amino acids, e.g., 1, 2, 3, 4, 5, 6, 7, 8, 9, or 10, from amino acids 250 to 286 of SEQ ID NO: 2 or amino acids 268 to 305 of SEQ ID NO: 4.

The carbohydrate binding module preferably comprises or consists of amino acids 250 to 286 of SEQ ID NO: 2 or amino acids 268 to 305 of SEQ ID NO: 4 or an allelic variant thereof; or is a fragment thereof having carbohydrate binding activity.

In another embodiment, the present invention also relates to carbohydrate binding modules encoded by polynucleotides that hybridize under medium stringency conditions, medium-high stringency conditions, high stringency conditions, or very high stringency conditions (as defined above) with (i) the nucleotides 875 to 985 of SEQ ID NO: 1, or the nucleotides 907 to 1020 of SEQ ID NO: 3, (ii) the cDNA sequence thereof, or (iii) the full-length complement of (i) or (ii) (Sambrook et al., 1989, supra).

In another embodiment, the present invention also relates to carbohydrate binding modules encoded by polynucleotides having a sequence identity to nucleotides 875 to 985 of SEQ ID NO: 1 of at least 80%, e.g., at least 85%, at least 90%, at least 91%, at least 92%, at least 93%, at least 94%, at least 95%, at least 96%, at least 97%, at least 98%, at least 99%, or 100%.

The polynucleotide encoding the carbohydrate binding module preferably comprises or consists of nucleotides 875 to 985 of SEQ ID NO: 1 or is the sequence contained in plasmid pGH45_Hya8473.

In another embodiment, the present invention also relates to carbohydrate binding modules encoded by polynucleotides having a sequence identity to nucleotides 907 to 1020 of SEQ ID NO: 3 of at least 85%, e.g., at least 90%, at least 91%, at least 92%, at least 93%, at least 94%, at least 95%, at least 96%, at least 97%, at least 98%, at least 99%, or 100%.

The polynucleotide encoding the carbohydrate binding module preferably comprises or consists of nucleotides 907 to 1020 of SEQ ID NO: 3 or is the sequence contained in plasmid pGH45_Thihy3331.

In another embodiment, the present invention also relates to carbohydrate binding module variants of amino acids 250 to 286 of SEQ ID NO: 2 or amino acids 268 to 305 of SEQ ID NO: 4 comprising a substitution, deletion, and/or insertion at one or more (e.g., several) positions. In one aspect, the number of amino acid substitutions, deletions and/or insertions introduced into the sequence of amino acids 250 to 286 of SEQ ID NO: 2 is up to 10, e.g., 1, 2, 3, 4, 5, 6, 8, 9, or 10.

A catalytic domain operably linked to the carbohydrate binding module may be from a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase. The polynucleotide encoding the catalytic domain may be obtained from any prokaryotic, eukaryotic, or other source.

Polynucleotides

The present invention also relates to isolated polynucleotides encoding a polypeptide, a catalytic domain, or carbohydrate binding module of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Humicola*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1 or SEQ ID NO: 3 or SEQ ID NO: 5 or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide.

The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff at al., 1978, *Proc. Natl. Acad. Sci. USA* 75: 3727-3731), as well as the tac promoter (DeBoer et al., 1983, *Proc. Natl. Acad. Sci, USA* 80: 21-25). Further promoters are described in "Useful proteins from recombinant bacteria" in Gilbert at al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus lichen/formic* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotides sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*, Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol, Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacterial.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbial. Methods* 64: 391-397) or conjugation (see, e.g., Pinedo and Smets, 2005, *Appl. Environ. Microbial.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol, Rev.* 45: 409-436). However, any method known in the art for introducing DNA into a host cell can be used.

The host cell may also be a eukaryote, such as a mammalian, insect, plant, or fungal cell.

The host cell may be a fungal cell, "Fungi" as used herein includes the phyla Ascomycota, Basidiomycota, Chytridiomycota, and Zygomycota as well as the Oomycota and all mitosporic fungi (as defined by Hawksworth et al., in, *Ainsworth and Bisby's Dictionary of The Fungi*, 8th edition, 1995, CAB International, University Press, Cambridge, UK).

The fungal host cell may be a yeast cell, "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium*

*bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiate, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen at al., 1988, *Bio/Technology* 6: 1419-1422. Suitable methods for transforming *Fusarium* species are described by Malardier et al., 1989, *Gene* 78: 147-156, and WO 96/00787, Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito at al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (h) recovering the polypeptide. In one aspect, the cell is a *Aspergillus* cell. In another aspect, the cell is a *Aspergillus oryzae* cell. In another aspect, the cell is *Aspergillus oryzae* HowB101 (WO 95/035385).

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides with endoglucanase activity. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu at al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu at al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil at al., 1992, *Bio/Technology* 10: 667-674). An alternative method for transformation of monocots is based on protoplast transformation as described by Omirulleh at al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Removal or Reduction of Endoglucanase Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene, By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having endoglucanase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the mature polypeptide coding sequence of SEQ ID NO: 1 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially endoglucanase-free product are of particular interest in the production of eukaryotic polypeptides, in particular fungal proteins such as enzymes. The endoglucanase-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from endoglucanase activity that is produced by a method of the present invention.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid (s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide of the present invention. Preferably, the compositions are enriched in such a polypeptide. The term "enriched" indicates that the endoglucanse activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulose, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Enzyme Composition for Textile

The present invention further relates to enzyme composition for textile comprising one or more polypeptide as defined in the present invention.

The textile composition may be adapted for specific uses, such as biostoning or biopolishing, which can provide at least one of the textile benefits as reduced pilling formation, reduced weight loss of fabric, increased abrasion effect, and low backstaining level.

The textile composition may further include one or more of the enzymes selected from the group consisting of catalase, proteases, lipases, cutinases, amylases, hemicellulases, pectinases, cellulases and peroxidases/oxidases.

The textile composition typically comprises conventional ingredients including without limitation other enzymes, as well as surfactants, stabilizer, wetting agent, dispersing agents, antifoaming agents, lubricants, builder systems, and the like, or a mixture thereof, that provide superior effects related to, e.g., strength, resistance to pilling, water absorbency, and dyeability.

The textile composition can be in any form, such as a solid, liquid, paste, gel or any combination thereof.

Uses

The present invention is also directed to the following methods of treating textile with the polypeptides having endoglucanase activity, or compositions thereof.

Biopolishing

The processing of a fabric, such as of a cellulosic material, into material ready for garment manufacturing involves several steps: spinning of the fiber into a yarn; construction of woven or knit fabric from the yarn; and subsequent preparation processes, dyeing/printing and finishing operations. Preparation processes are necessary for removing natural and man-induced impurities from fibers and for improving their aesthetic appearance and processability prior to for instance dyeing/printing and finishing. Common preparation processes comprise desizing (for woven goods), scouring, and bleaching, which produce a fabric suitable for dyeing or finishing.

Biopolishing is a method to treat cellulosic fabrics during their manufacturing by enzymes such as cellulases, which improves fabric quality with respect to "reduced pilling formation". The most important effects of biopolishing can be characterised by less fuzz and pilling, increased gloss/luster, improved fabric handle, increased durable softness and/or improved water absorbency. Biopolishing usually takes place in the wet processing of the manufacture of knitted and woven fabrics or garments. Wet processing comprises such steps as e.g., desizing, scouring, bleaching, washing, dying/printing and finishing. Biopolishing could be performed as a separate step after any of the wetting steps or in combination with any of those wetting steps. As used herein, the term "biopolishing", "depilling" and "anti-pilling" are interchangeable.

The present invention relates to a method for manufacturing textile, by treating textile with an isolated polypeptide having endoglucanase activity in a biopolishing process.

In one embodiment, the invention provides a method for obtaining a cellulosic or cellulose-containing textile having a reduced pilling formation, the method comprising treating textile with a polypeptide having endoglucanase activity in an aqueous solution. In this embodiment, the method of biopolishing can be applied to yarn, fabric or garment.

Biostoning

Some dyed fabric such as denim fabric, requires that the yarns are dyed before weaving. For denim fabric, the warp yarns are dyed for example with indigo, and sized before weaving. Preferably the dyeing of the denim yarn is a ring-dyeing. A preferred embodiment of the invention is ring-dyeing of the yarn with a vat dye such as indigo, or an indigo-related dye such as thioindigo, or a sulfur dye, or a direct dye, or a reactive dye, or a naphthol. The yarn may also be dyed with more than one dye, e.g., first with a sulphur dye and then with a vat dye, or vice versa.

Preferably, the yarns undergo scouring and/or bleaching before they are dyed, in order to achieve higher quality of denim fabric. In general, after woven into dyed fabric, such as denim, the dyed fabric or garment proceeds to a desizing stage, preferably followed by a biostoning step and/or a color modification step.

The present invention also relates to a method for manufacturing textile, by treating textile with an isolated polypeptide having endoglucanase activity in a biostoning process.

In one embodiment, the invention provides a method for introducing into the surface of dyed fabric or garment, localized variations in colour density in which the method comprises the step of contacting the fabric or garment with a polypeptide having endoglucanase activity as defined in the present invention. Preferably, the dyed fabric or garment is cellulosic or cellulose-containing fabric or garment. More preferably, the dyed fabric is a denim fabric, even more preferably, indigo dyed denim fabric. As used herein, the term "biostoning", "stone washing" and "abrasion" are interchangeable.

In another embodiment, the invention provides a denim manufacturing process, which comprises: a) desizing of the denim fabric; biostoning the denim with a polypeptide having endoglucanase activity; c) rinsing.

Signal Peptide

The present invention also relates to an isolated polynucleotide encoding a signal peptide comprising or consisting of amino acids 1 to 21 of SEQ ID NO: 2, amino acids 1 to 21 of SEQ ID NO: 4, amino acids 1 to 18 of SEQ ID NO: 6. The polynucleotides may further comprise a gene encoding a protein, which is operably linked to the signal peptide. The protein is preferably foreign to the signal peptide. In one aspect, the polynucleotide encoding the signal peptide is nucleotides 1 to 63 of SEQ ID NO: 1, nucleotides 1 to 63 of SEQ ID NO: 3, nucleotides 1 to 54 of SEQ ID NO: 5. The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The gene may be obtained from any prokaryotic, eukaryotic, or other source.

The present methods and compositions are further described in the following numbered paragraphs.

1. An isolated polypeptide having endoglucanase activity, selected from the group consisting of:
 (a) a polypeptide having at least 80% sequence identity to the mature polypeptide of SEQ ID NO: 2, or a polypeptide having at least 85% sequence identity to the mature polypeptide of SEQ ID NO: 4; a polypeptide having at least 85% sequence identity to the mature polypeptide of SEQ ID NO: 6;

(b) a polypeptide encoded by a polynucleotide that hybridizes under medium, stringency conditions with (i) the mature polypeptide coding sequence of SEQ ID NO: 1 or SEQ ID NO: 3 or SEQ ID NO: 5, (ii) the cDNA sequence thereof, or (iii) the full-length complement of (i) or (ii);

(c) a polypeptide encoded by a polynucleotide having at least 80% sequence identity to the mature polypeptide coding sequence of SEQ ID NO: 1 or encoded by a polynucleotide having at least 85% sequence identity to the mature polypeptide coding sequence of SEQ ID NO: 3, or encoded by a polynucleotide having at least 85% sequence identity to the mature polypeptide coding sequence of SEQ ID NO: 5, or the cDNA sequence thereof;

(d) a variant of the mature polypeptide of SEQ ID NO: 2 or SEQ ID NO: 4 or SEQ ID NO: 6 comprising a substitution, deletion, and/or insertion at one or more positions; and (e) a fragment of the polypeptide of (a), (b), (c), or (d) that has endoglucanase activity.

2. The polypeptide of paragraph 1, comprising or consisting of SEQ ID NO: 2 or SEQ ID NO: 4 or SEQ ID NO: 6, or the mature polypeptide of SEQ ID NO: 2 or SEQ ID NO: 4 or SEQ ID NO: 6.

3. The polypeptide of paragraph 2, wherein the mature polypeptide is amino acids 22 to 286 of SEQ ID NO: 2, amino acids 22 to 305 of SEQ ID NO: 4 or amino acids 19 to 222 of SEQ ID NO: 6.

4. The polypeptide of any of paragraphs 1-3, which is a variant of the mature polypeptide of SEQ ID NO: 2, SEQ ID NO: 4 or SEQ ID NO: 6 comprising a substitution, deletion, and/or insertion at one or more positions.

5. The polypeptide of paragraph 1, which is a fragment of SEQ ID NO: 2, SEQ ID NO: 4 or SEQ ID NO: 6, wherein the fragment has endoglucanase activity.

6. An isolated polypeptide comprising a catalytic domain selected from the group consisting of:

(a) a catalytic domain having at least 85% sequence identity to amino acids 22 to 237 of SEQ ID NO: 2, or at least 90% sequence identity to amino acids 22 to 223 of SEQ ID NO: 4, or at least 85% sequence identity to amino acids 21 to 222 of SEQ ID NO: 6;

(b) a catalytic domain encoded by a polynucleotide that hybridizes under medium stringency conditions with (i) nucleotides 64 to 838 of SEQ ID NO: 1 or nucleotides 64 to 774 of SEQ ID NO: 3, or nucleotides 61 to 835 of SEQ ID NO: 5, (ii) the cDNA sequence thereof, or (iii) the full-length complement of (i) or (ii);

(c) a catalytic domain encoded by a polynucleotide having at least 85% sequence identity to the catalytic domain of SEQ ID NO: 1 or at least 90% sequence identity to nucleotides 64 to 774 of SEQ ID NO: 3, or at least 85% sequence identity to nucleotides 61 to 835 of SEQ ID NO: 5, or the cDNA sequence thereof;

(d) a variant of amino acids 22 to 237 of SEQ ID NO: 2 or a variant of amino acids 22 to 223 of SEQ ID NO: 4, or at least 85% sequence identity to nucleotides 21 to 222 of SEQ ID NO: 6 comprising a substitution, deletion, and/or insertion at one or more positions; and (e) a fragment of the catalytic domain of (a), (b), (c), or (d) that has endoglucanase activity.

7. The polypeptide of paragraph 6, further comprising a carbohydrate binding module.

8. An isolated polypeptide comprising a carbohydrate binding module operably linked to a catalytic domain, wherein the binding domain is selected from the group consisting of:

(a) a carbohydrate binding module having at least 80% sequence identity to amino acids 250 to 286 of SEQ ID NO: 2 or at least 85% sequence identity to amino acids 268 to 305 of SEQ ID NO: 4;

(b) a carbohydrate binding module encoded by a polynucleotide that hybridizes under medium stringency conditions with (i) nucleotides 875 to 985 of SEQ ID NO: 1 or nucleotides 907 to 1020 of SEQ ID NO: 3, (ii) the cDNA sequence thereof, or (iii) the full-length complement of (i) or (ii);

(c) a carbohydrate binding module encoded by a polynucleotide having at least 80% sequence identity to nucleotides 875 to 985 of SEQ ID NO: 1 or at least 85% sequence identity to nucleotides 907 to 1020 of SEQ ID NO: 3, or the cDNA sequence thereof;

(d) a variant of amino acids 250 to 286 of SEQ ID NO: 2 or a variant of amino acids 268 to 305 of SEQ ID NO: 4 comprising a substitution, deletion, and/or insertion at one or more positions; and (e) a fragment of (a), (b), (c), or (d) that has carbohydrate binding activity.

9. The polypeptide of paragraph 6, wherein the catalytic domain is obtained from a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

10. The polypeptide of any of paragraphs 1-9, which is obtained from *Humicola*, preferably from *Humicola hyalothermophila*, or is obtained from *Thielavia*, preferably from *Thielavia hyrcaniae*.

11. A composition comprising the polypeptide of any of paragraphs 1-10.

12. An isolated polynucleotide encoding the polypeptide of any of paragraphs 1-10.

13. A nucleic acid construct or expression vector comprising the polynucleotide of paragraphs 12 operably linked to one or more control sequences that direct the production of the polypeptide in an expression host.

14. A recombinant host cell comprising the polynucleotide of paragraph 12 operably linked to one or more control sequences that direct the production of the polypeptide.

15. A method of producing the polypeptide of any of paragraphs 1-10, comprising cultivating a cell, which in its wild-type form produces the polypeptide, under conditions conducive for production of the polypeptide.

16. The method of paragraph 15, further comprising recovering the polypeptide.

17. A method of producing a polypeptide having endoglucanase activity, comprising cultivating the host cell of paragraph 14 under conditions conducive for production of the polypeptide.

18. The method of paragraph 17, further comprising recovering the polypeptide.

19. A transgenic plant, plant part or plant cell transformed with a polynucleotide encoding the polypeptide of any of paragraphs 1-10.

20. A method of producing a polypeptide having endoglucanase activity, comprising cultivating the transgenic Want or plant cell of paragraph 19 under conditions conducive for production of the polypeptide.

21. The method of paragraph 20, further comprising recovering the polypeptide.
22. A method for treating textile, by treating textile with the polypeptide of any of paragraphs 1-10.
23. The method of paragraph 22, wherein the method is applied in a biopolishing process.
24. The method of paragraph 22, wherein the method is applied in a biostoning process.
25. The method of any of paragraphs 22-24, wherein the method further comprises one or more enzymes selected from the group consisting of catalases, proteases, lipases, cutinases, amylases, hemicellulases, pectinases, cellulases and peroxidases.
26. The method of any of paragraphs 22-25, wherein the treating textile is manufacturing the textile.

The present invention is further described by the following examples that should not be construed as limiting the scope of the invention.

EXAMPLES

Materials

Chemicals used as buffers and substrates were commercial products of at least reagent grade.

Strain

The fungal strain CBS454.80 was used in the Examples. The strain CBS454.80 was identified as *Humicola hyalothermophila*, based on both morphological characteristics and ITS rDNA sequence.

Two fungal strain *Thielavia hyrcaniae* were isolated from a soil sample collected from China. The strains were identified as *Thielavia hyrcaniae* based on both morphological characteristics and ITS rDNA sequence.

Media

PDA medium was composed of 39 grams of potato dextrose agar and deionized water to 1 liter.

YPG medium contained 0.4% of yeast extract, 0.1% of $KH_2PO_4$, 0.05% of $MgSO_4.7H_2O$, 1.5% glucose in deionized water.

YPM medium contained 1% yeast extract, 2% of peptone, and 2% of maltose in deionized water.

Minimal medium plates were composed of 342 g of sucrose, 20 ml of salt solution (2.6% KCl, 2.6% $MgSO_4.7H_2O$, 7.6% $KH_2PO_4$, 2 ppm $Na_2B_4O_7.10H_2O$, 20 ppm $CuSO_4.5H_2O$, 40 ppm $FeSO_4.7H_2O$, 40 ppm $MnSO_4.2H_2O$, 40 ppm $Na_2MoO_4.2H_2O$, 400 ppm $ZnSO_4.7H_2O$), 20 g of agar, and deionized water to 1 liter.

pH 5.0 buffer with 50 mM acetate: 2.873 g sodium acetate and 0.901 g acetic acid were dissolved in 1 L de-ionized water;

pH 6.5 buffer with 50 mM phosphate: 5.642 g disodium hydrogen phosphate dodecahydrate ($Na_2HPO_4.12H_2O$) and 5.344 g sodium dihydrogen phosphate dehydrate ($NaH_2PO_4.2H_2O$) were dissolved in 1 L de-ionized water;

pH 7.5 buffer with 50 mM phosphate: 15.045 g disodium hydrogen phosphate dodecahydrate ($Na_2HPO_4.12H_2O$) and 1.248 g sodium dihydrogen phosphate dehydrate ($NaH_2PO_4.2H_2O$) were dissolved in 1 L de-ionized water;

pH 8.5 buffer with 50 mM phosphate: 17.607 g disodium hydrogen phosphate dodecahydrate ($Na_2HPO_4.12H_2O$) and 0.116 g potassium dihydrogen phosphate ($KH_2PO_4$) were dissolved in 1 L de-ionized water.

Enzymes

Cellusoft CR® (a mono-component *Thielavia terrestris* GH45 endoglucanase product, commercially available from Novozymes A/S)

Cellulase A (the mature peptide of a *Humicola insolens* endoglucanase shown as SEQ ID NO: 7 (produced according to WO 91/17243))

Fabrics

Cotton interlock: 405 bleached, HM-A0008, available from HM Cotton Co., td, Guangzhou, China.

Denim: batch No. L001, 7*7176*42, 12 oz., available from Hangzhou Yimei, Co., Ltd, China.

Method

Weight Loss Determination

The swatches were placed in the conditioned room (65%+/−5% humidity, 20+/−1° C.) for 24 hours before they were numbered, weighed by the analytical balance (for samples below 100 g) or a precision balance (for samples over 100 g) and recorded. After treatment, all samples were tumbled dried (AEG, LAVATHERM 37700, Germany) for 1 hour and conditioned for 24 hours in the conditioned room mentioned as above. For each sample, the weight loss was defined as below:

$$\text{Weight loss \%} = \frac{(\text{weight before} - \text{weight after}) * 100}{\text{weight before treatment}}$$

Pilling Notes Test

Fabrics including treated and untreated which had been pre-conditioned in norm climate (65% humidity, 21° C.) for at least 24 hours were tested for the pilling notes with Nu-Martindale Tester (James H. Heal Co. Ltd, England), with untreated fabrics of the same type as the abraded fabrics. A standard pilling test (Swiss Norm (SN) 198525) was carried out after 2000 Revolutions by marking from 1-5, with the meaning defined as below, where 1 shows poor anti-pilling and 5 shows excellent anti-pilling property. Thus the higher the Martindale pilling notes score the more effective the endoglucanase biopolishing treatment.

Note 5: No pilling
Note 4: Slight Pilling
Note 3: Moderate Pilling
Note 2: Distinct Pilling
Note 1: Heavy Pilling
½, ¼ notes are allowed To make the test result more reliable, 3 separate readings were carried out by different persons for each sample, and the average of the 3 readings was adopted as the final result of pilling notes.

Color Measurement for Denim

The abrasion level and backstaining level of the denim samples were determined by measuring the reflectance with pre-calibrated DataColor SF450X, alternatively an equivalent apparatus can be used. Four readings were taken for each sample, and the average of the readings were used. The abrasion level was evaluated with the index CIE L* on the blue side (front side) of the sample, and the backstaining level was evaluated with the index CIE b* on the back side of the sample.

L* indicates the change in white/black on a scale from 0 to 100, and a decrease in L* means an increase in black colour (decrease in white colour) and an increase in L* means an increase in white colour (decrease in black colour). Delta L* unit=L* of the swatch treated with a certain cellulase−L* of the swatch before cellulase treatment. The larger the Delta L* unit is the higher is the denim abrasion level, e.g. a Delta L* unit of 4 has higher abrasion level than Delta L* unit of 3.

b* indicates the change in blue/yellow, and a decrease in b* means an increase in blue colour (decrease in yellow colour), and an increase in b* means an increase in yellow colour (decrease in blue colour). Delta b* units=b* of the swatch treated with a certain cellulase–b* of the swatch before cellulase treatment. A larger Delta b* unit corresponds to a lower backstaining level, e.g. a Delta b* unit of −1.5 has lower backstaining level than the Delta b* unit of −2.5.

Protein Content

The enzyme protein in an enzyme product can be measured with BCA™ Protein Assay Kit (product number 23225, commercial available from Thermo Fisher Scientific Inc.) according to the product manual.

Example 1

Humicola Hyalothermophila Genomic DNA Extraction

Humicola hyalothermophila strain CBS454.80 was inoculated onto a PDA plate and incubated for 5 days at 25° C. in the darkness. Several mycelia-PDA plugs were inoculated into 500 ml shake flasks containing 100 ml of YPG medium. The flasks were incubated for 12 days at 25° C. with shaking at 160 rpm. The mycelia were collected by filtration through MIRACLOTH® (Calbiochem, La Jolla, Calif., USA) and frozen in liquid nitrogen. Frozen mycelia were ground, by a mortar and a pestle, to a fine powder, and genomic DNA was isolated using a DNeasy® Plant Maxi Kit (QIAGEN GmbH, Hilden, Germany).

Example 2

Genome Sequencing, Assembly and Annotation

The extracted genomic DNA samples were delivered to Beijing Genome Institute (BGI, Shenzhen, China) for genome sequencing using ILLUMINA® GA2 System (Illumina, Inc., San Diego, Calif., USA). The raw reads were assembled at BGI using in house program SOAPdenovo (Li et al., 2010, *Genome Research* 20(2): 265-72). The assembled sequences were analyzed using standard bioinformatics methods for gene finding and functional prediction. Briefly, geneID (Parra et al., 2000, *Genome Research* 10(4):511-515) was used for gene prediction. Blastall version 2.2.10 (National Center for Biotechnology Information (NCBI), Bethesda, Md., USA) and HMMER version 2.1.1 (National Center for Biotechnology Information (NCBI), Bethesda, Md., USA) were used to predict function based on structural homology. The family GH45 endoglucanase enzyme candidate was identified directly by analysis of the Blast results. Agene (Munch and Krogh, 2006, *BMC Bioinformatics* 7:263) and SignalP program (Bendtsen et al., 2004, *J. Mol. Biol.* 340: 783-795) were used to identify starting codons. Pepstats (European Bioinformatics Institute, Hinxton, Cambridge CB10 1SD, UK) was used to estimate isoelectric point of proteins, and molecular weight.

The genomic DNA and the deduced amino acid sequence of the *Humicola hyalothermophila* GH45 endoglucanase (GH45_Hya8473) is shown in SEQ ID NO: 1 and SEQ ID NO: 2 respectively. The coding sequence is nucleotide 1-988 including the stop codon TAA. The encoded predicted protein has 286 amino acids. Using the SignalP program, a signal peptide of 21 residues was predicted, which was further confirmed by the N-terminal sequencing showing mature peptide begins with ASGNGQS. The encoded protein contains 286 amino acids with endoglucanase catalytic domain of amino acids 22 to 237 and carbohydrate binding module of amino acids 250 to 286.

Example 3

Cloning of the *Humicola Hyalothermophila* GH45 Endoglucanase Gene from Genomic DNA One GH45 endoglucanase gene, GH45_Hya8473 (SEQ ID NO: 1 and SEQ ID NO: 2), was selected for expression cloning.

Based on the DNA information obtained from genome sequencing, oligonucleotide primers, shown below, were designed to amplify the GH45_Hya8473 gene from genomic DNA of *Humicola hyalothermophila* strain CBS454.80. Primers fabricated by Invitrogen (Invitrogen, Beijing, China).

```
Forward primer:
                                          (SEQ ID NO: 8)
5' ACACAACTGGGGATCC ACC atgcgttcttctcctatccttcgc
3'

Reverse primer:
                                          (SEQ ID NO: 9)
5' GTCACCCTCTAGATCT gccatctgacctcagcagaaca 3'
```

Lowercase characters in the forward primer represent the coding region of the gene and the flanking region of the gene in the reverse primer. The capitalized parts were homologous to the insertion sites of pPFJO355 vector which has been described in WO2011005867.

For each gene, 20 picomoles of primer pair each of the forward and reverse) were used in a PCR reaction composed of 2 microliter of *Humicola hyalothermophila* CBS454.80 genomic DNA, 10 microliter of 5× Phusion® GC Buffer, 1.5 microliter of DMSO, 2.5 mM each of dATP, dTTP, dGTP, and dCTP, and 0.6 unit of Phusion® High-Fidelity DNA Polymerase (Finnzymes Oy, Espoo, Finland) in a final volume of 50 microliter. The amplification was performed using a Peltier Thermal Cycler (MJ Research Inc., South San Francisco, Calif., USA) programmed for denaturing at 98° C. for 1 minutes; 6 cycles of denaturing at 98° C. for 40 seconds, annealing at 65° C. for 40 seconds, with 1° C. decrease per cycle and elongation at 72° C. for 1 minute; and another 25 cycles each at 94° C. for 40 seconds, 60° C. for 40 seconds and 72° C. for 1 minute; final extension at 72° C. for 10 minutes. The heat block then went to a 4° C. soak cycle.

The PCR products were isolated by 1.0% agarose gel electrophoresis using TBE buffer (90 mM Tris-borate and 1 mM EDTA) where a single product band around the expected size, 1.0 kb, was visualized under UV light. PCR products were then purified from solution by using an Illustra™ GFX™ FOR DNA and Gel Band Purification Kit (GE Healthcare, Buckinghamshire, UK) according to the manufacturer's instructions.

Plasmid pPFJO355 was digested with Bam HI and Bgl II, isolated by 1.0% agarose gel electrophoresis using TBE buffer, and purified using an Illustra™ GFX™ PCR DNA and Gel Band Purification Kit according to the manufacturer's instructions.

An In-Fusion™ Dry-down Mix (Clontech Laboratories, Inc., Mountain View, Calif., USA) was used to clone the fragment directly into the expression vector pPFJO355, without the need for restriction digestion and ligation.

The PCR products and the digested vector were ligated together using an In-Fusion™ Dry-down Mix resulting in plasmid: pGH45_Hya8473 (FIG. 1), in which transcription of *Humicola hyalothermophila* GH45 endoglucanase gene was under the control of a promoter from the gene of *Aspergillus oryzae* alpha-amylase. The cloning operation was according to the manufacturer's instruction. In brief, 30 ng of pPFJO355 digested with Bam HI and Bgl II, and 60 ng of the *Humicola hyalothermophila* GH45 endoglucanase gene FOR product were added to the reaction vial and resuspended the powder in a final volume of 10 microliter with addition of deionized water. The reaction was incubated at 37° C. for 15 minutes and than 50° C. for 15 minutes. Three microliter of the reaction were used to transform *E. coli* TOP10 competent cells (TIANGEN Biotech (Beijing) Co. Ltd., Beijing, China). *E. coli* transformants containing expression constructs were detected by colony PCR which is a method for quick screening of plasmid inserts directly from *E. coli* colonies. Briefly, in the premixed PCR solution aliquot in each PCR tube, including PCR buffer, $MgCl_2$, dNTP and primer pairs for which the PCR fragment generated, a single colony was added by picking up with a sterile tip and twirling the tip in the reaction solution. Normally 7-10 colonies were screened. After the FOR program, reactions were checked on agarose gel. The colony giving the amplification of expected size was possibly to contain the correct insert. The plasmid DNA was prepared using a QIAprep® Spin Miniprep Kit (QIAGEN GmbH, Hilden, Germany). The Humiceia hyalothemwhila GH45 endoglucanase gene inserted in pGH45_Hya8473 was confirmed by DNA sequencing using 3730XL DNA Analyzers (Applied Biosystems Inc, Foster City, Calif., USA).

Example 4

Expression of the *Humicola Hyalothermophila* GH45 Endoglucanase Gene in *Aspergillus oryzae*

*Aspergillus oryzae* HowB101 (WO 95/035385) protoplasts were prepared according to the method of Christensen et al., (1988, *Bio/Technology* 6: 1419-1422). HowB101 was transformed with 3 microgram of pGH45_Hya8473. The transformation yielded approximately 50 transformants. Eight transformants were isolated to individual Minimal medium plates.

Four transformants were inoculated separately into 3 ml of YPM medium in a 24-well plate and incubated at 30° C. with mixing at 150 rpm. After 3 days incubation, 20 microliter of supernatant from each culture were analyzed by SDS-PAGE using a NUPAGE® NOVEX® 4-12% Bis-Tris Gel with MES (Invitrogen Corporation, Carlsbad, Calif., USA) according to the manufacturer's instructions. The resulting gel was stained with INSTANTBLUE™ (Expedeon Ltd., Babraham Cambridge, UK). The SDS-PAGE profile of the culture showed that the *Humicola hyalothermophila* GH45 endoglucanase gene was expressed with protein band detected. The size of the major band was smeary at around 35 KD. The expression strain was designated as O8KVJ.

Example 5

Fermentation of *Aspergillus Oryzae* Expression Strain O8KVJ

A slant of O8KVJ was washed with 10 ml of YPM and inoculated into 8 flasks of 2 L containing 400 ml of YPM medium, shaking at 30 C, 80 rpm, to generate broth for characterization of the enzyme. The culture was harvested on day 3 and filtered using a 0.45 micrometer DURAPORE Membrane (Millipore, Bedford, Mass., USA).

Example 6

Purification of Recombinant *Humicola Hyalothermophila* GH45 Endoglucanase from *Aspergillus Oryzae* O8KVJ 3200 ml supernatant of the recombinant strain O8KVJ was precipitated with ammonium sulfate (80% saturation) and re-dissolved in 50 ml 20 mM NaAc buffer, pH5.5, then dialyzed against the same buffer and filtered through a 0.45 mm filter, the final volume was 80 ml. The solution was applied to a 40 ml Q SEPHAROSE® Fast Flow column (GE Healthcare, Buckinghamshire, UK) equilibrated in 20 mM NaAc buffer, pH5.5, and the proteins was eluted with a linear NaCl gradient (0-0.5M). Fractions eluted with 0.1-0.3M NaCl were collected and further purified on a 40 ml Phenyl Sepharose 6 Fast Flow column (GE 17-0965-05) with a linear $(NH_4)_2SO_4$ gradient (1.2-0 M). Fractions were evaluated by SDS-PAGE (NP0336BOX, NUPAGE 4-12% BT GEL 1.5MM15W), and the fractions containing a band of approximately 35 kDa were pooled. Then the pooled solution was concentrated by ultrafiltration.

Example 7

Endoglucanase Activity Assay 0.2% AZCL-HE-cellulose (Megazyme, I-AZCEL) was suspended in 20 mM Bis-Tris buffer of pH 6.0 with addition of 0.01% Triton X-100 by gentle stirring, which was used as substrate. Then 120 microliter substrate and 30 microliter enzyme sample of 1 mg/ml prepared according to Example 6 were mixed in a Microtiter plate and placed on ice before reaction. The assay was initiated by transferring the Microtiter plate to an Eppendorf thermomixer, which was set to the assay temperature of 50° C. The plate was incubated for 20 minutes on the Eppendorf thermomixer at its shaking rate 700 rpm for Microtiter plate. The incubation was stopped by transferring the plate back to the ice bath. Then the plate was centrifuged in an ice cold centrifuge for 5 minutes and 100 microliter supernatant was transferred to a microtiter plate. $OD_{595}$ was read as a measure of endo-cellulase activity. All reactions were done with triplicate and a buffer blind without adding any enzyme was included in the assay.

If $OD_{595}$ value of the enzyme sample minus $OD_{595}$ value of the blind is above 0, the enzyme is defined as the enzyme having endoglucanase activity.

$OD_{595}$ value of the *Humicola hyalothermophila* GH45 sample tested in this example minus $OD_{595}$ of the blind was above 0, which shows the *Humicola hyalothermophila* GH45 ins the present invention has the endoglucanase activity.

Example 8

Denim Abrasion with *Humicola Hyalothermophila* GH45 and Cellusoft CR in Launder-O-Meter The *Humicola hyalothermophila* GH45 endoglucanase (mature peptide of SEQ ID NO: 2) purified from Example 6 was used for denim abrasion in the present example. The commercially available product Cellusoft CR was also tested as the benchmark.

Raw denim was desized and cut to 16 cm wide and 24 cm long. The denim was cut and sewn, forming a tube with height of 12.5 cm and weight of about 18 g. The tubes were placed in a conditioned room (65% relative humidity, 21° C.) for 24 hours before they were numbered, weighed by the analytical balance and recorded. One conditioned tube was placed in each beaker, with the blue side facing inward. For each beaker, 30 big nuts (M6M-SR-A4-80, acid proof, M10 DIN 934), 10 small nuts (M6M-SR-A4-80, acid proof, M6 DIN 934), 7 big star magnets (diameter of 17 mm, item no. 3-CO-411117, Cowie, Schweiz via Bie & Berntsen), and 3 small star magnets (diameter of 14 mm, item no. 3-CO-11117, Cowie, Schweiz via Bie & Berntsen) were used to supply the mechanical aids. Then the buffers prepared as described in the media part and the enzyme solutions were added according to Table 1, based on the calculation of actual fabric weights, to make a total volume around 70 ml, which would create a liquid to fabric ratio of 3.8:1 (v/w).

The Launder-O-Meter (LOM) machine was started after the required program was chosen, and it would hold when the temperature reached the pre-set temperature, e.g. 35° C. or 55° C. Each beaker was fitted with a lid lined with 2 neoprin gaskets and close tightly with the metal clamping device. The beakers were loaded into the preheated LOU Metal racks were used to accommodate and secure 6 beakers, in the horizontal position, in each of the 4 drum positions. The LOM lid was closed and the washing program was continued and the timing was initiated. 2 hours later, all beakers were removed from LOM and the denim samples were transferred to the inactivation solution (2 g/L sodium carbonate) at 85° C. for 10 minutes. Then the swatches were rinsed in hot water for 2 times and in cold water for 2 times. The denim samples were tumble-dried (AEG, LAVA-THERM 37700, Germany) for 1 hour, and then conditioned at 65% relative humidity, 21° C. for 24 hours prior to evaluation.

The abrasion and backstaining level of the denim samples were determined by measuring the reflectance before and after the endoglucanase treatment with pre-calibrated Data-Color SF450X. For both L* and b*, four readings were taken for each fabric and the average of the four readings was used. The abrasion level was evaluated with the index CIE L* of the blue side of the sample, and the backstaining level was evaluated with the index CIE b* of the back of the sample.

As shown in Table 1, at 35° C., 0.064 mg/g fabric of Humicola hyalothermophila GH45 endoglucanase at pH 7.5 results in a higher abrasion level but similar backstaining level as compared to 0.086 mg/g fabric of Cellusoft CR at pH 6.5; at 55° C., 0.032 mg/g fabric of Humicola hyalothermophila GH45 endoglucanase at pH 7.5 delivers a similar denim abrasion level as 0.064 mg/g fabric of it does at 35° C., while 0.043 mg/g fabric of Cellusoft CR at pH 6.5 results in a much higher abrasion level than 0.064 mg/g fabric of it does at 35° C. Therefore, Humicola hyalothermophila GH45 endoglucanase delivers a more flat temperature curve in denim abrasion than Cellusoft CR. And to achieve a similar abrasion level, Humicola hyalothermophila GH45 endoglucanase causes a lower backstaining level.

TABLE 1

Denim abrasion by *Humicola hyalothermophila* GH45 endoglucanase and Cellusoft CR in LOM at 35 or 55° C., 2 hours

| Temperature (°C.) | Enzyme | Dosage (mg enzyme protein/g of fabric) | pH | delta L* | delta b* |
|---|---|---|---|---|---|
| 35 | *Humicola hyalothermophila* GH45 endoglucanase | 0.064 | 7.5 | 5.82 | 3.36 |
|  | Cellusoft CR | 0.086 | 6.5 | 4.19 | 3.37 |
| 55 | *Humicola hyalothermophila* GH45 endoglucanase | 0.032 | 7.5 | 5.92 | 3.63 |
|  | Cellusoft CR | 0.043 | 6.5 | 7.01 | 4.66 |

Note: average of triple samples for each condition.

Example 9

Biopolishing with *Humicola Hyalothermophila* GH45 Endoglucanase at Different pHs in Launder-O-Meter The *Humicola hyalothermophila* GH45 endoglucanase (mature peptide of SEQ ID NO: 2) purified from Example 6 was used for biopolishing in the present example.

Cotton fabric swatches were cut into about 16 cm*16 cm (about 5 grams each). The swatches were placed in the conditioned room (65% humidity, 21° C.) for 24 hours before they were numbered, weighed by the analytical balance and recorded. The biopolishing was conducted with a Launder-O-meter. Two conditioned swatches and 20 big steel balls (total weight of 220 grams) were placed in each beaker to supply the mechanical aids. The beaker was filled with enzymes according to Table 2 and buffers prepared as described in media part to a total volume of around 100 ml, which could get a liquid to fabric ratio of about 10:1 (v/w).

The LOM was operated similarly as Example 8 except that the 5 beakers were placed in a vertical position, in each of the 4 drum positions. After the treatment with 0.016 mg/g fabric of *Humicola hyalothermophila* GH45 endoglucanase at different pH at the pre-set temperature 55° C. for 1 hour, the swatches were removed from the beakers and transferred into the inactivation solution with 2 g/L of sodium carbonate and kept at 85° C. for 10 min. Then the swatches were rinsed in hot water for 2 times and in cold water for 2 times. And they were tumble-dried as Example 7 for 1 hour, conditioned for 24 hours at 65% relative humidity, 21° C. prior to evaluation in weight loss and pilling notes.

As summarized in table 2, *Humicola hyalothermophila* GH45 endoglucanase of the present invention works efficiently in biopolishing at pH 6.5 to pH 8.5 and best at pH 7.5.

TABLE 2

LOM biopolishing with *Humicola hyalothermophila* GH45 endoglucanase at 55° C.

| pH | Weight loss(%) | Pilling notes |
|---|---|---|
| 5 | 0.2 | 1.5 |
| 6.5 | 0.8 | 3.5 |
| 7.5 | 0.9 | 4.0 |
| 8.5 | 0.6 | 3.4 |

Example 10

Biopolishing with *Humicola hyalothermophila* GH45 Endoglucanase and Cellusoft CR at Different Temperatures in Launder-O-Meter The *Humicola hyalothermophila* GH45 endoglucanase (mature peptide of SEQ ID NO: 2) purified from Example 6 was extensively tested at different temperatures in the present example with Cellusoft CR as the benchmark.

The fabric preparation and trial operation was similar to Example 9 except that several independent trials with different temperatures/dosages were conducted in this example.

As summarized in table 3, *Humicola hyalothermophila* GH45 endoglucanase of the present invention was stronger than Cellusoft CR on protein basis: at 35° C., pH 6.5, 0.064 mg/g fabric of *Humicola hyalothermophila* GH45 endoglucanase delivers similar biopolishing performance as 0.087 mg/g fabric of Cellusoft CR; at 45° C., pH 7.5, 0.008 mg/g fabric of *Humicola hyalothermophila* GH45 endoglucanase delivers similar biopolishing performance as 0.022 mg/g fabric of Cellusoft CR at pH 6.5; at 55° C., pH 6.5, 0.016 mg/g fabric of *Humicola hyalothermophila* GH45 endoglucanase delivers better biopolishing performance as 0.022 mg/g fabric of Cellusoft CR. So in a broad range of temperature, it shows that *Humicola hyalothermophila* GH45 is stronger than Cellusoft CR in biopolishing on protein basis.

TABLE 3

LOM biopolishing with *Humicola hyalothermophila* GH45 endoglucanase and Cellusoft CR at different temperatures

| Temperature(° C.) | Enzyme | Dosage (mg enzyme protein/g of fabric) | pH | Weight loss(%) | Pilling notes |
|---|---|---|---|---|---|
| 35 | blank | 0.000 | 6.5 | 0.0 | 1.5 |
| | *Humicola hyalothermophila* GH45 endoglucanase | 0.064 | 6.5 | 1.5 | 3.6 |
| | Cellusoft CR | 0.087 | 6.5 | 0.9 | 3.6 |
| 45 | blank | 0.000 | 6.5 | 0.3 | 1.5 |
| | *Humicola hyalothermophila* GH45 endoglucanase | 0.008 | 7.5 | 0.7 | 3.1 |
| | | 0.016 | | 1.1 | 3.6 |
| | Cellusoft CR | 0.011 | 6.5 | 0.7 | 2.4 |
| | | 0.022 | | 1.1 | 3.1 |
| 55 | *Humicola hyalothermophila* GH45 endoglucanase | 0.016 | 7.5 | 0.9 | 4.0 |
| | Cellusoft CR | 0.022 | 6.5 | 1.2 | 3.1 |

Example 11

Biopolishing with *Humicola hyalothermophila* GH45 Endoglucanase, Cellusoft CR, Cellulase A with or without LAS in Launder-O-Meter The *Humicola hyalothermophila* GH45 endoglucanase (mature peptide of SEC) ID NO: 2) purified from Example 6 was tested for biopolishing with or without the presence of 0.2 g/L of linear alkylbenzene sulfonate (LAS) in the present example. Commercially available products Cellusoft CR and Cellulase A were also included as the benchmarks.

The fabric preparation and trial operation were similar to Example 9 except that in present example trial was conducted at 45° C. and pH 7.5 for *Humicola hyalothermophila* GH45 endoglucanase and pH 6.5 for the other two and 0.2 g/L of LAS was added in selected beakers. The dosage for each sample was specified in Table 4.

As summarized in table 4, *Humicola hyalothermophila* GH45 endoglucanase of the present invention works well at the presence of 0.2 g/L of LAS at pH 7.5, which indicates a good compatibility of this enzyme with this anionic surfactant. Cellusoft CR also shows a good compatibility with LAS, while in contrast an obvious performance drop is seen for Cellulase A when 0.2 g/L was applied together with the enzyme. So *Humicola hyalothermophila* GH45 endoglucanase is a cellulase with good compatibility with LAS during biopolishing step.

TABLE 4

LOM biopolishing with *Humicola hyalothermophila* GH45 endoglucanase, Cellusoft CR and Cellulase A with or without LAS at 45° C.

| Enzyme | pH | Dosage (mg enzyme protein/g) | LAS(g/L) | Weight loss(%) | Pilling notes |
|---|---|---|---|---|---|
| *Humicola hyalothermophila* GH45 endoglucanase | 7.5 | 0.032 | 0 | 1.4 | 3.5 |
| | 7.5 | 0.032 | 0.2 | 1.1 | 3.4 |
| Cellusoft CR | 6.5 | 0.043 | 0 | 1.6 | 3.9 |
| | 6.5 | 0.043 | 0.2 | 1.5 | 3.6 |
| Cellulase A | 6.5 | 0.053 | 0 | 1.6 | 4.0 |
| | 6.5 | 0.053 | 0.2 | 0.6 | 1.5 |

Example 12

Biopolishing with *Humicola hyalothermophila* GH45 Endoglucanase and Cellusoft CR with Salts/Dyestuff in Launder-O-Meter The *Humicola hyalothermophila* GH45 endoglucanase (mature peptide of SEQ ID NO: 2) purified from Example 6 was tested for biopolishing with salts and/or some representative dyestuff in the present example. Cellusoft CR was included as the benchmarks.

The fabric preparation and trial operation were similar to Example 9 except that in present example trial was conducted at 45° C. and pH 7.5 for *Humicola hyalothermophila* GH45 endoglucanase and pH 6.5 for Cellusoft CR and salts and dyestuff were also loaded in some selected beakers as specified in Table 5.

As summarized in table 5, *Humicola hyalothermophila* GH45 endoglucanase at pH 7.5 shows good compatibility with 80 of $Na_2SO_4$, or NaCl, or 5% Black 5, or 5% Blue 19, or the combination of 80 WI of $Na_2SO_4$ and 5% Black 5. So *Humicola hyalothermophila* GH45 endoglucanase is a cellulase with good compatibility with salts and/or dyestuff during biopolishing step.

TABLE 5

LOM biopolishing with *Humicola hyalothermophila* GH45 endoglucanase, Cellusoft CR with or without salts/dyestuff at 45° C.

| Enzyme | pH | Dosage(mg enzyme protein/g) | Salts | Dyestuff | Pilling notes |
|---|---|---|---|---|---|
| *Humicola hyalothermophila* | 7.5 | 0.032 | 0 | 0 | 3.6 |
| | 7.5 | 0.032 | 80 g/L | | 2.9 |

TABLE 5-continued

LOM biopolishing with *Humicola hyalothermophila* GH45 endoglucanase, Cellusoft CR with or without salts/dyestuff at 45° C.

| Enzyme | pH | Dosage(mg enzyme protein/g) | Salts | Dyestuff | Pilling notes |
|---|---|---|---|---|---|
| GH45 endoglucanase | 7.5 | 0.032 | Na₂SO₄ 80 g/L NaCl | | 2.8 |
| | 7.5 | 0.032 | | 5% Black 5 | 3.3 |
| | 7.5 | 0.032 | | 5% Blue 19 | 3.4 |
| | 7.5 | 0.032 | 80 g/L Na₂SO₄ | 5% Black 5 | 3.4 |
| Cellusoft CR | 6.5 | 0.043 | 0 | 0 | 3.8 |
| | 6.5 | 0.043 | 80 g/L Na₂SO₄ | | 2.0 |
| | 6.5 | 0.043 | 80 g/L NaCl | | 2.9 |
| | 6.5 | 0.043 | | 5% Black 5 | 3.6 |
| | 6.5 | 0.043 | | 5% Blue 19 | 1.8 |
| | 6.5 | 0.043 | 80 g/L Na₂SO₄ | 5% Black 5 | 2.3 |

Example 13

*Thielavia hyrcaniae* Genomic DNA Extraction

*Thielavia hyrcaniae* strain was inoculated onto a PDA plate and incubated for 5 days at 37° C. in the darkness. Several mycelia-PDA plugs were inoculated into 500 ml shake flasks containing 100 ml of YPG medium. The flasks were incubated for 6 days at 45° C. with shaking at 160 rpm. The mycelia were collected by filtration through MIRA-CLOTH® (Calbiochem, La Jolla, Calif., USA) and frozen in liquid nitrogen. Frozen mycelia were ground, by a mortar and a pestle, to a fine powder, and genomic DNA was isolated using a method developed Scott O. Rogers & Arnold J. Bendich (Plant Molecular Biology 5: 69-76, 1985).

Example 14

Genome Sequencing, Assembly and Annotation

The extracted genomic DNA samples were delivered to Berry Genomics company (Beijing, China) for genome sequencing using ILLUMINA® Hiseq2000 System (Illumina, Inc., San Diego, Calif., USA). The raw reads were assembled using program Abyss 1.2.7 (Simpson et al., 2009, Genome Research 19(6): 1117-1123) with k-mer 51 and quality score cutoff 16. The assembled sequences were analyzed using standard bioinformatics methods for gene finding and functional prediction. Briefly, geneID (Parra et al., 2000, *Genome Research* 10(4):511-515) was used for gene prediction. Blastall version 2.2.10 (National Center for Biotechnology Information (NCBI), Bethesda, Md., USA) and HMMER version 2.1.1 (National Center for Biotechnology Information (NCBI), Bethesda, Md., USA) were used to predict function based on structural homology. The family GH45 endoglucanase enzyme candidate was identified directly by analysis of the Blast results. Agene (Munch and Krogh, 2006, *BMC Bioinformatics* 7:263) and SignalP program (Bendtsen et 2004, *J. Mol. Biol.* 340: 783-795) were used to identify starting codons. SignalP was further used to estimate length of signal peptide. Pepstats (European Bioinformatics Institute, Hinxton, Cambridge CB10 1SD, UK) was used to estimate isoelectric point of proteins, and molecular weight.

The genomic DNA and the deduced amino acid sequence of the *Thielavia hyrcaniae* GH45 endoglucanase is shown in SEQ ID NO: 3 and SEQ ID NO: 4 respectively. The coding sequence is nucleotide 1-1023 including the stop codon. The encoded predicted protein has 305 amino acids. Using the SignalP program, a signal peptide of 21 residues was predicted, which was further confirmed by the N-terminal sequencing showing mature peptide begins with ADGK-STR. The encoded protein contains 305 amino acids with endoglucanase catalytic domain of amino acids 22 to 223 and carbohydrate binding module of amino acids 268 to 305.

Example 15

Cloning of the *Thielavia Hyrcaniae* GH45 Endoglucanase Gene from Genomic DNA

One GH45 endoglucanase gene, GH45_Thihy3331 (SEQ ID NO: 3 and SEQ ID NO: 4), was selected for expression cloning.

Based on the DNA information obtained from genome sequencing, oligonucleotide primers, shown below, were designed to amplify the GH45_Hya3331 gene from genomic DNA of *Thielavia hyrcaniae* strain. Primers fabricated by Invitrogen (Invitrogen, Beijing, China).

```
                                        (SEQ ID NO: 10)
Forward primer:
5' ACACAACTGGGGATCC ACC atgcgctcgactcccgttc 3'

(SEQ ID NO: 11)
Reverse primer:
5' GTCACCCTCTAGATCT cgccaaaaggggtagacgagtactc 3'
```

Lowercase characters in the forward primer represent the coding region of the gene and the flanking region of the gene in the reverse primer. The capitalized parts were homologous to the insertion sites of pPFJO355 vector which has been described in WO2011005867.

For each gene, 20 picomoles of primer pair (each of the forward and reverse) were used in a PCR reaction composed of 2 microliter of *Thielavia hyrcaniae* genomic DNA, 10 microliter of 5× Phusion® GC Buffer, 1.5 microliter of DMSO, 2.5 mM each of dATP, dTTP, dGTP, and dCTP, and 0.6 unit of Phusion® High-Fidelity DNA Polymerase (Finnzymes Oy, Espoo, Finland) in a final volume of 50 microliter. The amplification was performed using a Peltier Thermal Cycler (M J Research Inc., South San Francisco, Calif., USA) programmed for denaturing at 98° C. for 1 minutes; 6 cycles of denaturing at 98° C. for 40 seconds, annealing at 65° C. for 40 seconds, with 1° C. decrease per cycle and elongation at 72° C. for 1 minute; and another 25 cycles each at 94° C. for 40 seconds, 60° C. for 40 seconds and 72° C. for 1 minute; final extension at 72° C. for 10 minutes. The heat block then went to a 4° C. soak cycle.

The PCR products were isolated by 1.0% agarose gel electrophoresis using TBE buffer (90 mM Tris-borate and 1 mM EDTA) where a single product band around the expected size, 1.0 kb, was visualized under UV light. PCR products were then purified from solution by using an Illustra™ GFX™ PCR DNA and Gel Band Purification Kit (GE Healthcare, Buckinghamshire, UK) according to the manufacturer's instructions.

Plasmid pPFJO355 was digested with Bam HI and Bgl II, isolated by 1.0% agarose gel electrophoresis using TBE buffer, and purified using an Illustra™ GFX™ FOR DNA and Gel Band Purification Kit according to the manufacturer's instructions.

An In-Fusion™ Dry-down Mix (Clontech Laboratories, Inc., Mountain View, Calif., USA) was used to clone the fragment directly into the expression vector pPFJO355, without the need for restriction digestion and ligation.

Figure 2:
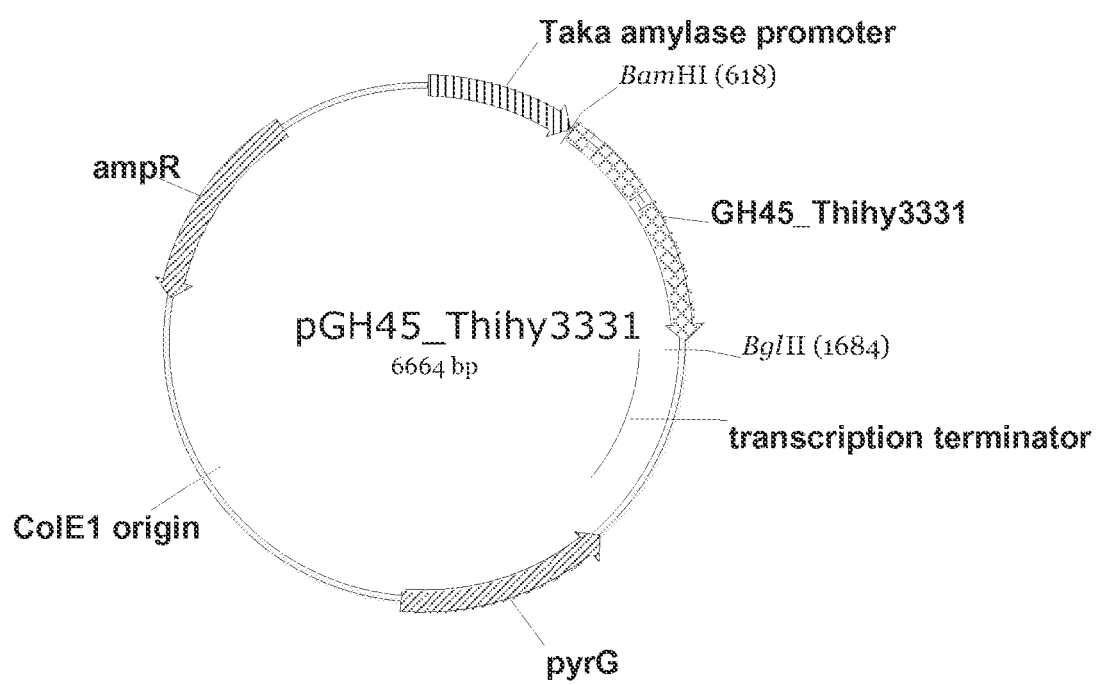
FIG. 2: DNA map of vector pGH45_Tihy3331 for expressing the *Thielavia hyrcaniae* GH45 endoglucanase gene.

The FOR products and the digested vector were ligated together using an In-Fusion™ Dry-down Mix resulting in plasmid: pGH45_Thihy3331 (FIG. 2), in which transcription of Thielavia hyrcaniae GH45 endoglucanase gene was under the control of a promoter from the gene of *Aspergillus oryzae* alpha-amylase. The cloning operation was according to the manufacturer's instruction. In brief, 30 ng of pPFJO355 digested with Bam HI and Bgl II, and 60 ng of the *Thielavia hyrcaniae* GH45 endoglucanase gene FOR product were added to the reaction vial and resuspended the powder in a final volume of 10 microliter with addition of deionized water. The reaction was incubated at 37° C. for 15 minutes and then 50° C. for 15 minutes. Three microliter of the reaction were used to transform *E. coli* TOP10 competent cells (TIANGEN Biotech (Beijing) Co, Ltd., Beijing, China), *E. coli* transformants containing expression constructs were detected by colony PCR which is a method for quick screening of plasmid inserts directly from *E. coli* colonies. Briefly, in the premixed PCR solution aliquot in each PCR tube, including FOR buffer, $MgCl_2$, dNTP and primer pairs for which the FOR fragment generated, a single colony was added by picking up with a sterile tip and twirling the tip in the reaction solution. Normally 7-10 colonies were screened. After the PCR program, reactions were checked on agarose gel. The colony giving the amplification of expected size was possibly to contain the correct insert. The plasmid DNA was prepared using a QIAprep® Spin Miniprep Kit (QIAGEN GmbH, Hilden, Germany). The *Thielavia hyrcaniae* GH45 endoglucanase gene inserted in pGH45_Thihy3331 was confirmed by DNA sequencing using 3730XL DNA Analyzers (Applied Biosystems Inc, Foster City, Calif., USA).

Example 16

Expression of the *Thielavia Hyrcaniae* GH45 Endoglucanase Gene in *Aspergillus oryzae*

*Aspergillus oryzae* HowB101 (WO 95/035385) protoplasts were prepared according to the method of Christensen at al., (1988, Bio/Technology 6: 1419-1422). HowB101 was transformed with 3 microgram of pGH45_Thihy3331. The transformation yielded approximately 50 transformants. Eight transformants were isolated to individual Minimal medium plates.

Four transformants were inoculated separately into 3 ml of YPM medium in a 24-well plate and incubated at 30° C. with mixing at 150 rpm, After 3 days incubation, 20 μl of supernatant from each culture were analyzed by SDS-PAGE using a NUPAGE® NOVEX® 4-12% Bis-Tris Gel with MES (Invitrogen Corporation, Carlsbad, Calif., USA) according to the manufacturer's instructions. The resulting gel was stained with INSTANTBLUE™ (Expedeon Ltd., Babraham Cambridge, UK). The SDS-PAGE profile of the culture showed that the *Thielavia hyrcaniae* GH45 endoglucanase gene was expressed with protein band detected. The size of the major band was smeary at around 45 KD. The expression strain was designated as O8KVN.

Example 17

Fermentation of *Aspergillus oryzae* Expression Strain O8KVN

A slant of O8KVN was washed with 10 ml of YPM and inoculated into 10 flasks of 2 L containing 400 ml of YPM medium, shaking at 30 C, 80 rpm, to generate broth for characterization of the enzyme. The culture was harvested on day 3 and filtered using a 0.45 micrometer DURAPORE Membrane (Millipore, Bedford, Mass., USA).

Example 18

Purification of Recombinant *Thielavia* Hyrcaniae GH45 Endoglucanase from *Aspergillus oryzae* O8KVN 4000 ml supernatant of the recombinant strain O8KVN was precipitated with ammonium sulfate (80% saturation) and re-dissolved in 50 ml 20 mM NaAc buffer, pH5.5, then dialyzed against the same buffer and filtered through a 0.45 mm filter, the final volume was 80 ml. The solution was applied to a 40 ml SEPHAROSE® Fast Flow column (GE Healthcare, Buckinghamshire, UK) equilibrated in 20 mM NaAc buffer, pH5.5, and the proteins was eluted with a linear NaCl gradient (0-0.5M), and the proteins unbound to the column were collected and further purified on a 40 ml Phenyl Sepharose 6 Fast Flow column (GE 17-0965-05) with a linear $(NH_4)_2SO_4$ gradient (1.2-0 M). Fractions were evaluated by SDS-PAGE (NP0336BOX, NUPAGE 4-12% BT GEL 1.5MM15W), and the fractions containing a band of approximately 45 kDa were pooled. Then the pooled solution was concentrated by ultrafiltration.

Example 19

Endoglucanase Activity Assay

Endoglucanase activity of *Thielavia hyrcaniae* GH45 (mature peptide of SEQ ID NO: 4) was tested according to the assay in Example 7.

$OD_{595}$ value of the *Thielavia hyrcaniae* GH45 sample tested in this example minus $OD_{595}$ of the blind was above 0, which shows the *Thielavia hyrcaniae* GH45 (mature peptide of SEQ ID NO: 4) in the present invention has the endoglucanase activity.

Example 20

Denim Abrasion with *Thielavia* Hyrcaniae GH45 Endoglucanase GH45_Thihy3331 Launder-O-Meter The *Thielavia hyrcaniae* GH45 endoglucanase GH45_Thihy3331 (mature peptide of SEQ ID NO: 4) purified from Example 18 was used for denim abrasion in the present example.

Raw denim was desized and cut to 16 cm wide and 24 cm long. The denim was cut and sewn, forming a tube with height of 12.5 cm and weight of about 18 g. The tubes were placed in a conditioned room (65% relative humidity, 21° C.) for 24 hours before they were numbered, weighed by the analytical balance and recorded. One conditioned tube was placed in each beaker, with the blue side facing inward. For each beaker, 30 big nuts (M6M-SR-A4-80, acid proof, M10 DIN 934), 10 small nuts (M6M-SR-A4-80, acid proof, M6 DIN 934), 7 big star magnets (diameter of 17 mm, item no. 3-CO-411117, Cowie, Schweiz via Bie & Berntsen), and 3 small star magnets (diameter of 14 mm, item no. 3-CO-11117, Cowie, Schweiz via Bie & Berntsen) were used to supply the mechanical aids. Then the buffers prepared as described in the media part and the enzyme solutions were added according to Table 6, based on the calculation of actual fabric weights, to make a total volume around 70 ml, which would create a liquid to fabric ratio of 3.8:1 (v/w).

The Launder-O-Meter (LOM) machine was started after the required program was chosen, and it would hold when the temperature reached the pre-set temperature, e.g. 35° C. or 55° C. Each beaker was fitted with a lid lined with 2 neoprin gaskets and close tightly with the metal clamping device. The beakers were loaded into the preheated LOM. Metal racks were used to accommodate and secure 6 beakers, in the horizontal position, in each of the 4 drum positions. The LOM lid was closed and the washing program was continued and the timing was initiated. 2 hours later, all beakers were removed from LOM and the denim samples were transferred to the inactivation solution (2 g/L sodium carbonate) at 85° C. for 10 minutes. Then the swatches were rinsed in hot water for 2 times and in cold water for 2 times. The denim samples were tumble-dried (AEG, LAVA-THERM 37700, Germany) for 1 hour, and then conditioned at 21° C., 65% relative humidity for 24 hours prior to evaluation.

The abrasion and backstaining level of the denim samples were determined by measuring the reflectance before and after the endoglucanse treatment with pre-calibrated DataColor SF450X. For both L* and b*, four readings were taken for each fabric and the average of the four readings was used. The abrasion level was evaluated with the index CIE L* of the blue side of the sample, and the backstaining level was evaluated with the index CIE b* of the back of the sample.

As shown in Table 6, the *Thielavia hyrcaniae* GH45 endoglucanase GH45-Thihy3331 results in obvious abrasion effect on denim fabrics at the dosage of 0.064 mg enzyme/g of fabric. And its denim abrasion performance is stable in the temperature range of 35 to 55° C., which offers more operation flexibility for customers in stone washing.

TABLE 6

Denim abrasion by GH45_Thihy3331 in LOM at 35 or 55° C., 2 hours

| Temperature(° C.) | Dosage (mg enzyme protein/ g of fabric) | pH | delta L* | delta b* |
|---|---|---|---|---|
| 35 | 0.064 | 6.5 | 6.99 | −3.59 |
| 55 | 0.064 | 6.5 | 6.54 | −4.17 |

Note:
average of triple samples for each condition.

Example 21

Biopolishing with *Thielavia* Hyrcaniae GH45 Endoglucanase GH45_Thihy3331 at Different pHs in Launder-O-Meter The *Thielavia hyrcaniae* GH45 endoglucanase GH45_Thihy3331 (mature peptide of SEQ ID NO: 4) purified from Example 18 was used for biopolishing at different pHs in the present example.

Cotton fabric swatches were cut into about 16 cm*16 cm (about 5 grams each). The swatches were placed in the conditioned room (65% humidity, 21° C.) for 24 hours before they were numbered, weighed by the analytical balance and recorded. The biopolishing was conducted with a Launder-O-meter. Two conditioned swatches and 20 big steel balls (total weight of 220 grams) were placed in each beaker to supply the mechanical aids. The beaker was filled with enzymes according to Table 2 and buffers prepared as described in media part to a total volume of around 100 ml, which could get a liquid to fabric ratio of about 10:1 (v/w).

The LOM was operated similarly as Example 20 except that the 5 beakers were placed in a vertical position, in each of the 4 drum positions. After the treatment with 0.032 mg/g fabric of GH45_Thihy3331 at different pH at the pre-set temperature 55° C. for 1 hour, the swatches were removed from the beakers and transferred into the inactivation solution with 2 g/L of sodium carbonate and kept at 85° C. for 10 min. Then the swatches were rinsed in hot water for 2 times and in cold water for 2 times. And they were tumble-dried as Example 20 for 1 hour, conditioned for 24 hours at 21° C., 65% relative humidity prior to evaluation in weight loss and pilling notes.

As summarized in Table 7, *Thielavia hyrcaniae* GH45 endoglucanase of the present invention works efficiently in cotton biopolishing at pH 6.5 to pH 8.5 and best at pH 6.5 to pH 7.5.

TABLE 7

LOM biopolishing with *Thielavia hyrcaniae* GH45 endoglucanase GH45_Thihy3331 at 55° C. and different pHs

| pH | Dosage (mg enzyme protein/ g of fabric) | Weight loss(%) | Pilling notes |
|---|---|---|---|
| 6.5 | 0.032 | 0.8 | 3.3 |
| 7.5 | 0.032 | 0.6 | 3.3 |
| 8.5 | 0.032 | 0.3 | 2.6 |

Example 22

Biopolishing with *Thielavia hyrcaniae* GH45 Endoglucanase GH45_Thihy3331 at Different Temperatures in Launder-O-Meter The *Thielavia hyrcaniae* GH45 endoglucanase GH45_Thihy3331 (mature peptide of SEQ ID NO: 4) purified from Example 18 was used for biopolishing at different temperatures in the present example.

The fabric preparation and LOM operation were similar to Example 21 except that in present example, pH was fixed at 6.5 while 3 different temperatures were applied in 3 separate trials.

As summarized in Table 8, *Thielavia hyrcaniae* GH45 endoglucanase GH45_Thihy3331 of the present invention works effectively in cotton biopolishing in a broad temperature range from 35 to 55° C. at pH 6.5.

TABLE 8

LOM biopolishing with *Thielavia hyrcaniae* GH45 endoglucanase GH45_Thihy3331 at different temperatures

| Temperature(° C.) | Dosage(mg enzyme protein/ g of fabric) | Weight loss(%) | Pilling notes |
|---|---|---|---|
| 35 | 0 | 0.0 | 1.5 |
| 35 | 0.032 | 0.6 | 2.1 |
| 35 | 0.064 | 1.1 | 3.1 |
| 45 | 0 | 0.0 | 1.5 |
| 45 | 0.032 | 0.8 | 3.0 |
| 55 | 0 | 0.0 | 1.5 |
| 55 | 0.032 | 1.6 | 3.9 |

Example 23

*Thielavia hyrcaniae* Genomic DNA Extraction

*Thielavia hyrcaniae* strain was inoculated onto a FDA plate and incubated for 5 days at 37° C. in the darkness, Several mycelia-PDA plugs were inoculated into 500 ml shake flasks containing 100 ml of YPG medium. The flasks were incubated for 6 days at 45° C. with shaking at 160 rpm. The mycelia were collected by filtration through MIRA-CLOTH® (Calbiochem, La Jolla, Calif., USA) and frozen in liquid nitrogen. Frozen mycelia were ground, by a mortar and a pestle, to a fine powder, and genomic DNA was isolated using a method developed by Scott O. Rogers & Arnold J. Bendich (Plant Molecular Biology 5: 69-76, 1985).

Example 24

Genome Sequencing, Assembly and Annotation

The extracted genomic DNA samples were delivered to BerryGenomics company (Beijing, China) for genome sequencing using ILLUMINA® Hiseq2000 System (Illumine, Inc., San Diego, Calif., USA). The raw reads were assembled using program Abyss 1.2.7 (Simpson et al., 2009, *Genome Research* 19(6): 1117-1123) with k-mer 51 and quality score cutoff 16. The assembled sequences were analyzed using standard bioinformatics methods for gene finding and functional prediction. Briefly, geneID (Parra et al., 2000, *Genome Research* 10(4):511-515) was used for gene prediction. Blastall version 2.2.10 (National Center for Biotechnology Information (NCBI), Bethesda, Md., USA) and HMMER version 2.1.1 (National Center for Biotechnology Information (NCBI), Bethesda, Md., USA) were used to predict function based on structural homology. The family GH45 endoglucanase enzyme candidate was identified directly by analysis of the Blast results. Agene (Munch and Krogh, 2006, *BMC Bioinformatics* 7:263) and SignalP program (Bendtsen et al., 2004, *J. Mol. Biol*, 340: 783-795) were used to identify starting codons. SignalP was further used to estimate length of signal peptide. Pepstats (European Bioinformatics Institute, Hinxton, Cambridge CB10 1SD, UK) was used to estimate isoelectric point of proteins, and molecular weight.

The genomic DNA and the deduced amino acid sequence of the *Thielavia hyrcaniae* GH45 endoglucanase is shown in SEQ ID NO: 5 and SEQ ID NO: 6 respectively. The coding sequence is nucleotide 1-838 including the stop codon. The encoded predicted protein has 222 amino acids. Using the SignalP program, a signal peptide of 18 residues was predicted, which was further confirmed by the N-terminal sequencing showing mature peptide begins with QATGKTT. The encoded protein contains 222 amino acids with endoglucanase catalytic domain of amino acids 21 to 222.

Example 25

Cloning of the *Thielavia hyrcaniae* GH45 Endoglucanase Gene from Genomic DNA

One GH45 endoglucanase gene, GH45_Thihy0507 (SEQ ID NO 5 and SEQ ID NO 6), was selected for expression cloning.

Based on the DNA information obtained from genome sequencing, oligonucleotide primers, shown below, were designed to amplify the GH45_Thihy0507 gene from genomic DNA of *Thielavia hyrcaniae* strain. Primers fabricated by Invitrogen (Invitrogen, Beijing, China).

```
                                         (SEQ ID NO: 12)
Forward primer:
5' ACACAACTGGGGATCC ACC atgcatctccccctg 3'

(SEQ ID NO: 13)
Reverse primer:
5' GTCACCCTCTAGATCT attcaccatcgcatacagccac 3'
```

Lowercase characters in the forward primer represent the coding region of the gene and the flanking region of the gene in the reverse primer. The capitalized parts were homologous to the insertion sites of pPFJO355 vector which has been described in WO2011005867.

For each gene, 20 picomoles of primer pair (each of the forward and reverse) were used in a PCR reaction composed of 2 microliter of *Thielavia hyrcaniae* genomic DNA, 10 microliter of 5× Phusion® GC Buffer, 1.5 microliter of DMSO, 2.5 mM each of dATP, dTTP, dGTP, and dCTP, and 0.6 unit of Phusion® High-Fidelity DNA Polymerase (Finnzymes Oy, Espoo, Finland) in a final volume of 50 microliter. The amplification was performed using a Peltier Thermal Cycler (MJ Research Inc., South San Francisco, Calif., USA) programmed for denaturing at 98° C. for 1 minutes; 6 cycles of denaturing at 98° C. for 40 seconds, annealing at 65° C. for 40 seconds, with 1° C. decrease per cycle and elongation at 72° C. for 1 minute; and another 25 cycles each at 94° C. for 40 seconds, 60° C. for 40 seconds and 72° C. for 1 minute; final extension at 72° C. for 10 minutes. The heat block then went to a 4° C. soak cycle.

The PCR products were isolated by 1.0% agarose gel electrophoresis using TBE buffer (90 mM Tris-borate and 1 mM EDTA) where a single product band around the expected size, 0.9 kb, was visualized under UV light. PCR products were then purified from solution by using an Illustra™ GFX™ PCR DNA and Gel Band Purification Kit (GE Healthcare, Buckinghamshire, UK) according to the manufacturer's instructions.

Plasmid pPFJO355 was digested with Bam HI and Bgl II, isolated by 1.0% agarose gel electrophoresis using TBE buffer, and purified using an Illustra™ GFX™ FOR DNA and Gel Band Purification Kit according to the manufacturer's instructions.

An In-Fusion™ Dry-down Mix (Clontech Laboratories, Inc., Mountain View, Calif., USA) was used to clone the fragment directly into the expression vector pPFJO355, without the need for restriction digestion and ligation.

Figure 3:
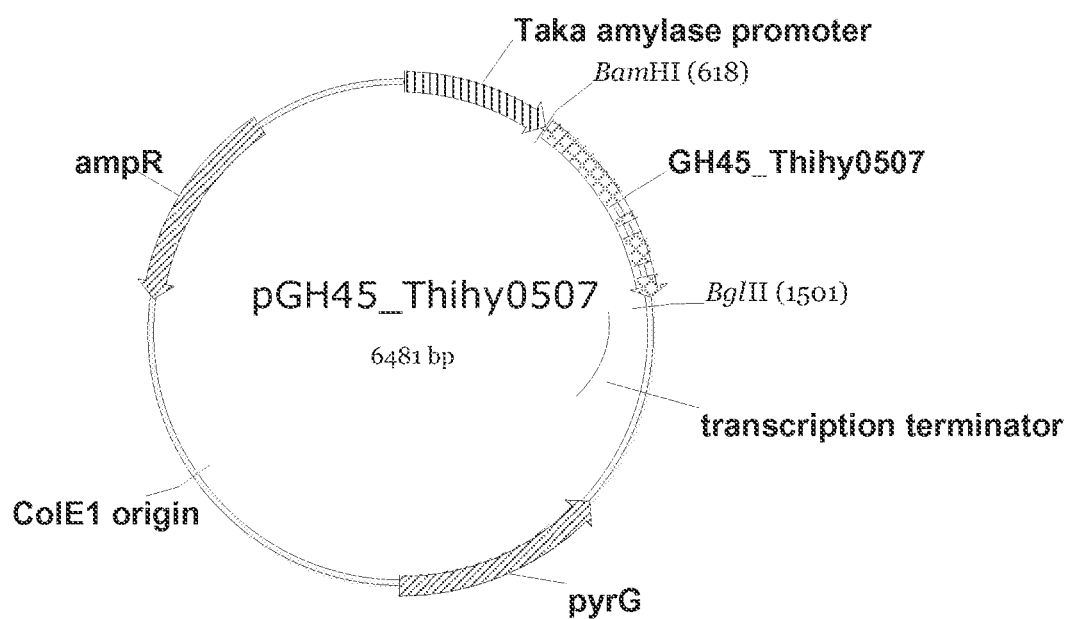
FIG. 3: DNA map of vector pGH45_Thihy0507 for expressing the *Thielavia hyrcaniae* GH45 endoglucanase gene.

The PCR products and the digested vector were ligated together using In-Fusion™ Dry-down Mix resulting in plasmid: pGH45_Thihy0507 (FIG. 3), in which transcription of *Thielavia hyrcaniae* GH45 endoglucanase gene was under the control of a promoter from the gene of *Aspergillus oryzae* alpha-amylase. The cloning operation was according to the manufacturer's instruction. In brief, 30 ng of pPFJO355 digested with Bam HI and Bgl II, and 60 ng of the *Thielavia hyrcaniae* GH45 endoglucanase gene PCR product were added to the reaction vial and resuspended the powder in a final volume of 10 microliter with addition of deionized water. The reaction was incubated at 37° C. for 15 minutes and then 50° C. for 15 minutes. Three microliter of the reaction were used to transform *E. coli* TOP10 competent cells (TIANGEN Biotech (Beijing) Co. Ltd., Beijing, China). *E. coli* transformants containing expression constructs were detected by colony PCR which is a method for quick screening of plasmid inserts directly from *E. coli* colonies. Briefly, in the premixed FOR solution aliquot in each FOR tube, including FOR buffer, MgCl2, dNTP and primer pairs for which the FOR fragment generated, a single colony was added by picking up with a sterile tip and twirling the tip in the reaction solution. Normally 7-10 colonies were screened. After the PCR program, reactions were checked on agarose gel. The colony giving the amplification of expected size was possibly to contain the correct insert. The plasmid DNA was prepared using a QIAprep® Spin Miniprep Kit (QIAGEN GmbH, Hilden, Germany). The *Thielavia hyrcaniae* GH45 endoglucanase gene inserted in pGH45_Thihy0507 was confirmed by DNA sequencing using 3730XL DNA Analyzers (Applied Biosystems Inc, Foster City, Calif., USA).

Example 26

Expression of the *Thielavia Hyrcaniae* GH45 Endoglucanase Gene in *Aspergillus oryzae*

*Aspergillus oryzae* HowB101 (WO 95/035385) protoplasts were prepared according to the method of Christensen et al., (1988, *Bio/Technology* 6: 1419-1422). HowB101 was transformed with 3 microgram of pGH45_Thihy0507. The transformation yielded approximately 50 transformants. Eight transformants were isolated to individual Minimal medium plates.

Four transformants were inoculated separately into 3 ml of YPM medium in a 24-well plate and incubated at 30° C. with mixing at 150 rpm, After 3 days incubation, 20 µl of supernatant from each culture were analyzed by SDS-PAGE using a NUPAGE® NOVEX® 4-12% Bis-Tris Gel with MES (Invitrogen Corporation, Carlsbad, Calif., USA) according to the manufacturer's instructions. The resulting gel was stained with INSTANTBLUE™ (Expedeon Ltd., Babraham Cambridge, UK). The SDS-PAGE profile of the culture showed that the *Thielavia hyrcaniae* GH45 endoglucanase gene was expressed with protein band detected. The size of the 2 major bands were around 25-30 KD. The expression strain was designated as O8KVP.

Example 27

Fermentation of *Aspergillus oryzae* Expression Strain O8KVP

A slant of O8KVP was washed with 10 ml of YPM and inoculated into 10 flasks of 2 L containing 400 ml of YPM medium, shaking at 30 C, 80 rpm, to generate broth for characterization of the enzyme. The culture was harvested on day 3 and filtered using a 0.45 micrometer DURAPORE Membrane (Millipore, Bedford, Mass., USA).

Example 28

Purification of Recombinant *Thielavia hyrcaniae* GH45 Endoglucanase from *Aspergillus oryzae* O8KVP 4000 ml supernatant of the recombinant strain O8KVP was precipitated with ammonium sulfate (80% saturation) and re-dissolved in 150 ml 20 mM Bis-Tris buffer, pH6.0, and filtered through a 0.45 mm filter. The solution was applied to a 40 ml Phenyl Sepharose 6 Fast Flow column (17-0965-05, GE Healthcare, Buckinghamshire, UK), proteins were eluted with a linear $(NH_4)_2SO_4$ gradient (1.2-0 M), and the proteins unbound to the column were collected and further purified on a 40 ml Q FF column (GE) equilibrated in 20 mM Bis-Tris buffer, pH6.0 with a linear NaCl gradient (0-0.5M). Fractions were evaluated by SDS-PAGE (NP0336BOX, NUPAGE 4-12% BT GEL 1.5MM15W), and the fractions containing a band of approximately 25 kDa were pooled. Then the pooled solution was concentrated by ultrafiltration.

Example 29

Endoglucanase Activity Assay

Endoglucanase activity of *Thielavia hyrcaniae* GH45 (mature peptide of SEQ ID NO: 6) was tested according to the assay in Example 7.

$OD_{595}$ value of the *Thielavia hyrcaniae* GH45 (mature peptide of SEQ ID NO: 6) tested in this example minus $OD_{595}$ of the blind was above 0, which shows the *Thielavia hyrcaniae* GH45 in the present invention has the endoglucanase activity.

Example 30

Biopolishing with *Thielavia hyrcaniae* GH45 Endoglucanase GH45_Thihy0507 Launder-O-Meter The *Thielavia hyrcaniae* GH45 endoglucanase GH45_Thihy0507 (mature peptide of SEQ ID NO: 6) purified from Example 28 was used for biopolishing in the present example.

Cotton fabric swatches were cut into about 16 cm*16 cm (about 5 grams each). The swatches were placed in the conditioned room (65% humidity, 21° C.) for 24 hours before they were numbered, weighed by the analytical balance and recorded. The biopolishing was conducted with a Launder-O-meter. Two conditioned swatches and 20 big steel balls (total weight of 220 grams) were placed in each beaker to supply the mechanical aids. The beaker was filled with enzymes according to Table 9 and buffers prepared as described in media part to a total volume of around 100 ml, which could get a liquid to fabric ratio of about 10:1 (v/w).

The Launder-O-Meter (LOM) machine was started after the required program was chosen, and it would hold when the temperature reached the pre-set temperature, e.g. 35° C., 45° C. or 55° C. Each beaker was fitted with a lid lined with 2 neoprin gaskets and close tightly with the metal clamping device. The beakers were loaded into the preheated LOM. Metal racks were used to accommodate and secure 5 beakers, in the vertical position, in each of the 4 drum positions. The LOM lid was closed and the washing program was continued and the timing was initiated. 1 hour later, all beakers were removed from LOM and the fabric samples were transferred to the inactivation solution (2 g/L sodium carbonate) at 85° C. for 10 minutes. Then the swatches were rinsed in hot water for 2 times and in cold water for 2 times. The fabric samples were tumble-dried (AEG, LAVATHERM 37700, Germany) for 1 hour, and then conditioned at 21° C., 65% relative humidity for 24 hours prior to evaluation in weight loss and pilling notes.

As shown in Table 9, the *Thielavia hyrcaniae* GH45 endoglucanase GH45-Thihy0507 results in weight loss and delivers anti-pilling effects on cotton fabrics in a broad temperature range from 35° C. to 55° C. at pH 6.5. It performed best at 35° C. to 45° C., at which 0.064 mg/g of GH45-Thihy0507 led a pilling note close to 3.0 while on contrast at 55° C. 0.128 mg/g of GH45-Thihy0507 was needed to achieve similar pilling notes.

TABLE 9

LOM biobpolishing with *Thielavia hyrcaniae* GH45 GH45_Thihy0507 at different temperatures, pH 6.5, 60 min

| Temperature(° C.) | Dosage(mg enzyme protein/ g of fabric) | Weight loss(%) | Pilling notes |
|---|---|---|---|
| 35 | 0.000 | 0.0 | 1.5 |
| 35 | 0.064 | 0.5 | 2.8 |
| 35 | 0.128 | 1.0 | 3.1 |
| 45 | 0.000 | 0.0 | 1.6 |
| 45 | 0.064 | 0.5 | 2.9 |
| 55 | 0.000 | 0.0 | 1.8 |
| 55 | 0.064 | 0.0 | 1.5 |
| 55 | 0.128 | 1.4 | 2.9 |
| 55 | 0.192 | 2.4 | 3.9 |

Example 31

Biopolishing with *Thielavia Hyrcaniae* GH45 Endoglucanase GH45_Thihy0507 at Different pHs in Launder-O-Meter The *Thielavia hyrcaniae* GH45 endoglucanase GH45_Thihy0507 (mature peptide of SEQ ID NO: 6) purified from Example 28 was used for biopolishing at different pHs in the present example.

The fabric preparation and LOM operation were similar to Example 30 except that in present example, temperature was fixed at 55° C. while different pHs were applied.

As summarized in Table 10, the *Thielavia hyrcaniae* GH45 endoglucanase of the present invention works efficiently in cotton biopolishing at pH 5 to pH 8.5 and best at pH 5 to pH 7.5. In 1 hour treatment at 55° C., 0.256 mg/g of the endoglucanase lead a pilling notes of 3.8 to 4.1 in the pH range from 5 to 7.5 and 2.5 at pH 8.5.

TABLE 10

LOM biopolishing with *Thielavia hyrcaniae* GH45 endoglucanase GH45_Thihy0507 at 55° C. and different pHs

| pH | Dosage(mg enzyme protein/ g of fabric) | Weight loss(%) | Pilling notes |
|---|---|---|---|
| 5 | 0.256 | 1.1 | 4.1 |
| 6.5 | 0.256 | 1.2 | 3.8 |
| 7.5 | 0.256 | 0.5 | 3.8 |
| 8.5 | 0.256 | 0.1 | 2.5 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A process of producing a polypeptide having endoglucanase activity, comprising:
   (a) culturing a recombinant microbial host cell under conditions conducive for producing the polypeptide, wherein the recombinant microbial host cell is transformed with a vector comprising a polynucleotide encoding the polypeptide, the polynucleotide is operably linked to one or more control sequences that direct the production of the polypeptide in the recombinant microbial host cell, and the amino acid sequence of the polypeptide is at least 85% identical to the sequence of amino acids 22 to 286 of SEQ ID NO: 2; and
   (b) recovering the polypeptide.

2. The process of claim 1, wherein the amino acid sequence of the polypeptide is at least 90% identical to the sequence of amino acids 22 to 286 of SEQ ID NO: 2.

3. The process of claim 1, wherein the amino acid sequence of the polypeptide is at least 95% identical to the sequence of amino acids 22 to 286 of SEQ ID NO: 2.

4. The process of claim 1, wherein the amino acid sequence of the polypeptide is at least 97% identical to the sequence of amino acids 22 to 286 of SEQ ID NO: 2.

5. The process of claim 1, wherein the polypeptide comprises the sequence of amino acids 22 to 286 of SEQ ID NO: 2.

6. The process of claim 1, wherein the polypeptide is a variant of the sequence of amino acids 22 to 286 of SEQ ID NO: 2, the variant has endoglucanase activity, and the amino acid sequence of the variant is at least 85% identical to the sequence of amino acids 22 to 286 of SEQ ID NO: 2.

7. The process of claim 1, wherein the polypeptide is a fragment of the sequence of amino acids 22 to 286 of SEQ ID NO: 2, the fragment has endoglucanase activity, and the amino acid sequence of the fragment is at least 85% identical to the sequence of amino acids 22 to 286 of SEQ ID NO: 2.

8. The process of claim 1, wherein at least one control sequence is heterologous.

9. The process of claim 1, wherein the recombinant microbial host cell is a filamentous fungal host cell selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* and *Trichoderma* cells.

10. The process of claim 2, wherein the recombinant microbial host cell is a filamentous fungal host cell selected from the group consisting of *Acremonium, Aspergillus, Aureobasidium, Bjerkandera, Ceriporiopsis, Chrysospo-*

*rium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, and *Trichoderma* cells.

11. The process of claim 3, wherein the recombinant microbial host cell is a filamentous fungal host cell selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, and *Trichoderma* cells.

12. The process of claim 4, wherein the recombinant microbial host cell is a filamentous fungal host cell selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, and *Trichoderma* cells.

13. A process of producing a polypeptide having endoglucanase activity, comprising:
    (a) culturing a recombinant microbial host cell under conditions conducive for producing the polypeptide, wherein the recombinant microbial host cell is transformed with a vector comprising a polynucleotide encoding the polypeptide, the polynucleotide is operably linked to one or more control sequences that direct the production of the polypeptide in the recombinant microbial host cell, and the polypeptide comprises a catalytic domain, wherein the catalytic domain has endoglucanase activity and the amino acid sequence of the catalytic domain is at least 90% identical to the sequence of amino acids 22 to 237 of SEQ ID NO: 2; and
    (b) recovering the polypeptide.

14. The process of claim 13, wherein the amino acid sequence of the catalytic domain is at least 95% identical to the sequence of amino acids 22 to 237 of SEQ ID NO: 2.

15. The process of claim 13, wherein the polypeptide further comprises a carbohydrate binding module that is heterologous to the catalytic domain.

16. A process of producing a polypeptide having cellulose binding activity, comprising:
    (a) culturing a recombinant microbial host cell under conditions conducive for producing the polypeptide, wherein the recombinant microbial host cell is transformed with a vector comprising a polynucleotide encoding the polypeptide, the polynucleotide is operably linked to one or more control sequences that direct the production of the polypeptide in the recombinant microbial host cell, and the polypeptide comprises a cellulose binding domain, wherein the cellulose binding domain has cellulose binding activity and the amino acid sequence of the cellulose binding domain is at least 85% identical to the sequence of amino acids 250 to 286 of SEQ ID NO: 2; and
    (b) recovering the polypeptide.

17. The process of claim 16, wherein the amino acid sequence of the cellulose binding domain is at least 90% identical to the sequence of amino acids 250 to 286 of SEQ ID NO: 2.

18. The process of claim 16, wherein the amino acid sequence of the cellulose binding domain is at least 95% identical to the sequence of amino acids 250 to 286 of SEQ ID NO: 2.

19. The process of claim 16, wherein the polypeptide further comprises a catalytic domain obtained from a hydrolase, isomerase, ligase, lyase, oxidoreductase, or transferase, wherein the catalytic domain is heterologous to the cellulose binding domain.

20. The process of claim 19, wherein the catalytic domain is obtained from an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

* * * * *